(12) United States Patent
Coon et al.

(10) Patent No.: US 8,092,545 B2
(45) Date of Patent: Jan. 10, 2012

(54) KNEE ARTHROPLASTY PROSTHESIS METHOD

(75) Inventors: Thomas M. Coon, Redding, CA (US); Alfred J. Tria, Jr., Princeton, NJ (US); Donald M. Smucker, Perrysburg, OH (US); Richard R. Van Zile, Bryan, OH (US)

(73) Assignee: Zimmer, Inc., Warsaw, IN (US)

( * ) Notice: Subject to any disclaimer, the term of this patent is extended or adjusted under 35 U.S.C. 154(b) by 1376 days.

(21) Appl. No.: 11/209,931

(22) Filed: Aug. 22, 2005

(65) Prior Publication Data

US 2005/0283250 A1    Dec. 22, 2005

Related U.S. Application Data

(62) Division of application No. 10/370,154, filed on Feb. 19, 2003, now abandoned.

(60) Provisional application No. 60/358,174, filed on Feb. 20, 2002.

(51) Int. Cl.
*A61F 2/38* (2006.01)
(52) U.S. Cl. .................... 623/20.32; 623/20.34
(58) Field of Classification Search .... 623/20.32–20.34, 623/20.15, 20.16, 20.27, 20.28, 20.29, 20.31, 623/20.35, 20.36
See application file for complete search history.

(56) References Cited

U.S. PATENT DOCUMENTS

| 1,201,992 | A | 10/1916 | Twaits |
|---|---|---|---|
| 2,007,980 | A | 7/1935 | Neumann |
| 2,355,935 | A | 8/1944 | White |
| 2,431,294 | A | 11/1947 | Dumlage |
| 2,521,421 | A | 9/1950 | Spranger |
| 2,682,287 | A | 6/1954 | Rollins, Jr. |
| 2,682,589 | A | 6/1954 | Dillon |
| 2,718,953 | A | 9/1955 | Pociask, Jr. |
| 2,725,878 | A | 12/1955 | Reiter |
| 2,768,329 | A | 10/1956 | Smith |
| 4,081,866 | A | 4/1978 | Upshaw et al. |
| 4,217,666 | A | 8/1980 | Averill |
| 4,224,696 | A | 9/1980 | Murray et al. |
| 4,309,778 | A | 1/1982 | Buechel et al. |
| 4,340,978 | A | 7/1982 | Buechel et al. |
| 4,470,158 | A | 9/1984 | Pappas et al. |
| 4,479,271 | A | 10/1984 | Bolesky et al. |
| 4,502,161 | A | 3/1985 | Wall |

(Continued)

FOREIGN PATENT DOCUMENTS

DE    3 917 285 A1    11/1990

(Continued)

OTHER PUBLICATIONS

European Search Report from PCT/US03/04750 which corresponds to this U.S. application.

(Continued)

*Primary Examiner* — Paul Prebilic
(74) *Attorney, Agent, or Firm* — Baker & Daniels LLP

(57) ABSTRACT

A knee arthroplasty prosthesis includes a femoral component having multiple pieces with engagement means provided for engaging various pieces of the femoral component to one another following their insertion in the incised area of the femur. A tibial component includes multiple pieces designed for assembly following positioning in the incision. The tibial component includes a Morse taper cavity on one piece of the tibial component and a Morse taper extension on another member of the component for receipt therein.

5 Claims, 19 Drawing Sheets

U.S. PATENT DOCUMENTS

| | | | |
|---|---|---|---|
| 4,627,853 A | 12/1986 | Campbell et al. | |
| 4,822,362 A | 4/1989 | Walker | |
| 4,822,366 A | 4/1989 | Bolesky | |
| 4,936,853 A | 6/1990 | Fabian | |
| 4,938,769 A | 7/1990 | Shaw | |
| 4,944,757 A * | 7/1990 | Martinez et al. | 623/20.15 |
| 5,007,933 A * | 4/1991 | Sidebotham et al. | 623/20.27 |
| 5,019,103 A * | 5/1991 | Van Zile et al. | 623/20.34 |
| 5,037,439 A | 8/1991 | Albrektsson et al. | |
| 5,061,271 A | 10/1991 | Van Zile | |
| 5,092,895 A | 3/1992 | Albrektsson et al. | |
| 5,100,409 A | 3/1992 | Coates et al. | |
| 5,116,375 A | 5/1992 | Hofmann | |
| 5,122,144 A | 6/1992 | Bert et al. | |
| 5,123,928 A | 6/1992 | Moser | |
| 5,147,406 A | 9/1992 | Houston et al. | |
| 5,147,407 A | 9/1992 | Tager | |
| 5,176,684 A | 1/1993 | Ferrante et al. | |
| 5,181,925 A | 1/1993 | Houston et al. | |
| 5,226,916 A | 7/1993 | Goodfellow et al. | |
| 5,258,032 A | 11/1993 | Bertin | |
| 5,275,603 A * | 1/1994 | Ferrante et al. | 606/86 R |
| 5,282,868 A | 2/1994 | Bahler | |
| 5,290,313 A | 3/1994 | Heldreth | |
| 5,312,411 A | 5/1994 | Steele et al. | |
| 5,330,534 A | 7/1994 | Herrington et al. | |
| 5,358,529 A | 10/1994 | Davidson | |
| 5,358,530 A | 10/1994 | Hodorek | |
| 5,364,397 A | 11/1994 | Hayes et al. | |
| 5,405,395 A | 4/1995 | Coates | |
| 5,405,398 A | 4/1995 | Bufford, III et al. | |
| 5,413,605 A | 5/1995 | Ashby et al. | |
| 5,489,311 A * | 2/1996 | Cipolletti | 623/20.34 |
| 5,528,032 A | 6/1996 | Uchiyama | |
| 5,549,684 A | 8/1996 | Amino et al. | |
| 5,549,688 A | 8/1996 | Ries et al. | |
| 5,556,433 A | 9/1996 | Gabriel et al. | |
| 5,569,259 A | 10/1996 | Ferrante et al. | |
| 5,609,641 A | 3/1997 | Johnson | |
| 5,609,645 A | 3/1997 | Vinciguerra | |
| 5,658,341 A | 8/1997 | Delfosse | |
| 5,702,464 A | 12/1997 | Lackey et al. | |
| 5,702,466 A | 12/1997 | Pappas et al. | |
| 5,725,584 A | 3/1998 | Walker et al. | |
| 5,728,162 A | 3/1998 | Eckhoff | |
| 5,755,801 A | 5/1998 | Walker et al. | |
| 5,755,803 A | 5/1998 | Haines et al. | |
| 5,766,255 A | 6/1998 | Slamin et al. | |
| 5,769,855 A | 6/1998 | Bertin et al. | |
| 5,776,201 A | 7/1998 | Colleran et al. | |
| 5,782,925 A | 7/1998 | Collazo et al. | |
| 5,824,103 A | 10/1998 | Williams | |
| 5,824,105 A | 10/1998 | Ries et al. | |
| 5,871,545 A | 2/1999 | Goodfellow et al. | |
| 5,876,456 A | 3/1999 | Sederholm et al. | |
| 5,876,459 A | 3/1999 | Powell | |
| 5,879,391 A | 3/1999 | Slamin | |
| 5,902,340 A | 5/1999 | White et al. | |
| 5,906,643 A | 5/1999 | Walker | |
| 5,911,758 A | 6/1999 | Oehy et al. | |
| 5,928,286 A | 7/1999 | Ashby et al. | |
| 5,964,808 A | 10/1999 | Blaha | |
| 5,976,147 A | 11/1999 | Lasalle | |
| 6,013,103 A | 1/2000 | Kaufman et al. | |
| 6,077,270 A | 6/2000 | Katz | |
| 6,090,146 A | 7/2000 | Rozow, III et al. | |
| 6,102,951 A | 8/2000 | Sutter et al. | |
| 6,123,729 A | 9/2000 | Insall et al. | |
| 6,126,693 A | 10/2000 | O'Neil et al. | |
| 6,132,468 A | 10/2000 | Mansmann | |
| 6,165,222 A | 12/2000 | Hoeppner et al. | |
| 6,165,223 A * | 12/2000 | Metzger et al. | 623/20.27 |
| 6,168,629 B1 | 1/2001 | Timoteo | |
| 6,171,340 B1 | 1/2001 | McDowell | |
| 6,171,342 B1 | 1/2001 | O'Neil et al. | |
| 6,190,415 B1 | 2/2001 | Cooke et al. | |
| 6,197,064 B1 | 3/2001 | Haines et al. | |
| 6,214,051 B1 | 4/2001 | Badorf et al. | |
| 6,214,052 B1 | 4/2001 | Burkinshaw | |
| 6,214,952 B1 | 4/2001 | Sadatoshi et al. | |
| 6,235,060 B1 | 5/2001 | Kubein-Meesenburg et al. | |
| 6,238,435 B1 | 5/2001 | Meulink et al. | |
| 6,245,110 B1 | 6/2001 | Grundei et al. | |
| 6,299,645 B1 | 10/2001 | Ogden | |
| 6,306,138 B1 * | 10/2001 | Clark et al. | 606/65 |
| 6,306,172 B1 | 10/2001 | O'Neil | |
| 6,364,911 B1 | 4/2002 | Schmotzer et al. | |
| 6,383,222 B1 | 5/2002 | Badorf | |
| 6,402,786 B1 | 6/2002 | Insall et al. | |
| 6,413,279 B1 * | 7/2002 | Metzger et al. | 623/20.29 |
| 6,428,577 B1 | 8/2002 | Evans et al. | |
| 6,436,142 B1 | 8/2002 | Paes et al. | |
| 6,482,209 B1 | 11/2002 | Engh et al. | |
| 6,485,519 B2 * | 11/2002 | Meyers et al. | 623/20.24 |
| 6,506,216 B1 | 1/2003 | McCue et al. | |
| 6,589,283 B1 | 7/2003 | Metzger et al. | |
| 6,669,728 B2 | 12/2003 | Despres et al. | |
| 6,719,800 B2 | 4/2004 | Meyers et al. | |
| 6,743,258 B1 | 6/2004 | Keller | |
| 6,749,638 B1 | 6/2004 | Saladino | |
| 6,896,702 B2 * | 5/2005 | Collazo | 623/20.16 |
| 6,972,039 B2 | 12/2005 | Metzger et al. | |
| 7,115,131 B2 | 10/2006 | Engh et al. | |
| 7,615,081 B2 | 11/2009 | Justin et al. | |
| 2001/0016778 A1 | 8/2001 | Badorf et al. | |
| 2002/0022890 A1 | 2/2002 | Jacobsson et al. | |
| 2002/0072799 A1 | 6/2002 | Despres, III et al. | |
| 2002/0138150 A1 | 9/2002 | Leclercq | |
| 2002/0198528 A1 | 12/2002 | Engh | |
| 2003/0004577 A1 | 1/2003 | Running | |
| 2003/0009232 A1 * | 1/2003 | Metzger et al. | 623/20.29 |
| 2003/0028196 A1 | 2/2003 | Bonutti | |
| 2003/0074078 A1 * | 4/2003 | Doubler et al. | 623/22.42 |
| 2003/0093156 A1 | 5/2003 | Metzger et al. | |
| 2003/0153977 A1 | 8/2003 | Suguro et al. | |
| 2003/0153979 A1 | 8/2003 | Hughes et al. | |
| 2003/0158606 A1 | 8/2003 | Coon et al. | |
| 2003/0204263 A1 | 10/2003 | Justin et al. | |
| 2003/0220697 A1 | 11/2003 | Justin et al. | |
| 2003/0225457 A1 | 12/2003 | Justin et al. | |
| 2003/0225458 A1 | 12/2003 | Donkers et al. | |
| 2004/0002767 A1 * | 1/2004 | Wyss | 623/20.27 |
| 2004/0073315 A1 | 4/2004 | Justin et al. | |
| 2004/0102582 A1 | 5/2004 | Dang et al. | |
| 2004/0117023 A1 | 6/2004 | Gerbec et al. | |
| 2004/0117024 A1 | 6/2004 | Gerbec et al. | |
| 2004/0143336 A1 | 7/2004 | Burkinshaw | |
| 2004/0249467 A1 | 12/2004 | Meyers et al. | |
| 2005/0107884 A1 | 5/2005 | Johnson et al. | |
| 2005/0203631 A1 | 9/2005 | Daniels et al. | |
| 2005/0203632 A1 | 9/2005 | Daniels | |
| 2005/0278034 A1 | 12/2005 | Johnson et al. | |
| 2005/0283250 A1 | 12/2005 | Coon et al. | |
| 2005/0283251 A1 | 12/2005 | Coon et al. | |
| 2005/0283252 A1 | 12/2005 | Coon et al. | |
| 2005/0283253 A1 | 12/2005 | Coon et al. | |
| 2006/0004460 A1 | 1/2006 | Engh et al. | |
| 2006/0155380 A1 | 7/2006 | Clemow et al. | |
| 2007/0162145 A1 | 7/2007 | Justin et al. | |
| 2008/0027563 A1 | 1/2008 | Johnson et al. | |
| 2008/0097576 A1 * | 4/2008 | Meyers et al. | 623/20.29 |
| 2008/0147203 A1 | 6/2008 | Cronin et al. | |
| 2009/0187251 A1 | 7/2009 | Justin et al. | |

FOREIGN PATENT DOCUMENTS

| | | |
|---|---|---|
| DE | 695 28 655 T2 | 1/1995 |
| DE | 197 16 879 A1 | 4/2002 |
| EP | 0 336 774 A1 | 4/1989 |
| EP | 0 376 658 A3 | 12/1989 |
| EP | 0 502 737 B1 | 3/1992 |
| EP | 0 522 822 B1 | 7/1992 |
| EP | 0552950 A | 7/1993 |
| EP | 0552950 A1 | 7/1993 |
| EP | 0 600 806 B1 | 6/1994 |
| EP | 0 731 676 B1 | 11/1994 |
| EP | 0 781 117 B1 | 9/1995 |
| EP | 0 674 887 B1 | 10/1995 |

| | | | |
|---|---|---|---|
| EP | 0 714 645 B1 | 11/1995 |
| EP | 773756 | 8/1996 |
| EP | 0 552 950 B1 | 9/1996 |
| EP | 0 749 734 B1 | 12/1996 |
| EP | 0 850 606 A | 12/1997 |
| EP | 0 913 136 A3 | 10/1998 |
| EP | 0 916 322 A2 | 10/1998 |
| EP | 1 348 408 A2 | 12/1998 |
| EP | 0 941 719 A2 | 3/1999 |
| EP | 0 985 386 A2 | 9/1999 |
| EP | 0 986 994 A2 | 9/1999 |
| EP | 0 956 836 A1 | 11/1999 |
| EP | 0 891 756 A2 | 10/2000 |
| EP | 1059070 | 12/2000 |
| EP | 913135 A3 | 1/2001 |
| EP | 913135 B1 | 1/2001 |
| EP | 1 216 669 A3 | 12/2001 |
| EP | 1 245 204 A3 | 10/2002 |
| EP | 1245204 A2 | 10/2002 |
| EP | 1352622 A2 | 10/2003 |
| EP | 1 380 273 A2 | 1/2004 |
| FR | 2 521 421 A | 8/1983 |
| FR | 2 682 287 | 11/1991 |
| FR | 2 682 589 A | 4/1993 |
| FR | 2716618 A1 | 9/1995 |
| FR | 2 718 953 | 10/1995 |
| FR | 2 768 329 | 9/1997 |
| FR | 2748389 | 11/1997 |
| FR | 2768329 A1 | 3/1999 |
| FR | 2799115 A1 | 4/2001 |
| GB | 2 007 980 | 5/1979 |
| GB | 2 355 935 A | 5/2001 |
| JP | 2002-291779 A | 10/2002 |
| WO | WO 87/02882 A1 | 5/1987 |
| WO | WO 89/11837 | 12/1989 |
| WO | WO 91/06260 | 5/1991 |
| WO | WO 98/02116 A1 | 1/1998 |
| WO | WO 98/08467 | 3/1998 |
| WO | WO 98/20818 A1 | 5/1998 |
| WO | WO 99/13803 A2 | 3/1999 |
| WO | WO 99/32053 | 7/1999 |
| WO | WO 00/23010 | 4/2000 |
| WO | WO 00/23011 A1 | 4/2000 |
| WO | WO 00/72784 | 12/2000 |
| WO | WO 01/06961 A1 | 1/2001 |
| WO | WO 01/34069 A1 | 5/2001 |
| WO | WO 01/70142 A1 | 9/2001 |
| WO | WO 02/07647 | 1/2002 |
| WO | WO 03/070127 A1 | 8/2003 |
| WO | WO 2004/037119 A2 | 5/2004 |

OTHER PUBLICATIONS

Geometric Total Knee; A-97-A-100.
Knee Systems; Insall/Burstein II* Modular Knee System; A 168-A 170.
The Miller/Galante Advantage; Unicompartmental Knee System; Zimmer.
Miller/Galante; Unicompartmental Knee System Implants and Instrumentation; Zimmer.
P.F.C. Total Knee System; Johnson & Johnson Orthopaedics. Implants.
The Intermedics Natural-Knee® System with Cancellous-Structured Titamium™.
Whiteside Ortholoc Modular Knee System; Surgical Procedure for the Whiteside Ortholoc® Modular Knee System; Dow Corning Wright.
Surgical Technique; The Intermedics Natural-Knee System; Aaron A. Hofmann, M.D., Associate Professor of Surgery, Division of Orthopedic Surgery, University of Utah Medical Center, Salt Lake City, Utah; Intermedics Orthopedics.
AGC Total Knee System; Patellar Femoral Systems; Biomet Inc.
Surgical Technique; Genesis Total Knee System Posterior-Stabilized; Smith +Nephew; Richards.
The AMK Total Knee system; Design Rationale and Surgical Procedure, Gerald A. Engh, M.D., John R. Moreland, M.D., Robert G. Volz, M.D.; Instruments Designed by John R. Moreland, M.D.; DePuy.
The Intermedics Natural Knee® System with Cancellous-Structured Titanium.
P.F.C. Total Knee System; Johnson & Johnson Orthopaedics; Tibial Component.
Patellar Resurfacing with Specialist Instruments in Total Knee Arthroplasty; Surgical Technique; Technique and Instruments Developed in Conjunction with James A. Rand, M.D., Mayo Clinic; Johnson & Johnson Orthopaedics.
International Preliminary Examination Report mailed Apr. 26, 2004 in related International application No. PCT/US2003/04750.
Wright Medical Technology, Inc. Advantim Total Knee System, MK 442-496, 1996.
Biomet, Inc., Maxim The Complete Knee System, Y-BMT-394/041595/M, 1995.
Hvid, et al., Trabecular bone Strength Patterns at the Proximal Tibial Epiphysis, Journal of Orthopaedic Research, vol. 3, No. 4, pp. 464-472, 1985—Abstract.
Stern, et al., The Effect of Tibial Stem Design on Component Micromotion in Knee Arthroplasty, Clinical Orthopaedics and Related Research, vol. 345, pp. 44-52, Dec. 1997—Abstract.
Lonner, et al., Changes in Bone Density After Cemented Total Knee Arthroplasty: Influence of Stem Design, The Journal of Arthroplasty, vol. 16, No. 1, pp. 107-111, Jan. 2001—Abstract.
Brochure—Zimmer NexGen MIS Tibial Component, 97-5950-001-00 7.5mm, 2005, 2006.
Brochure—Zimmer NexGen System, Complete Knee Solution, Implant Options—Surgeon-Specific.
Brochure—Zimmer Natural-Knee II System, 97-6299-001-00 10mm 2005.
Office Action mailed Jun. 30, 2009 in related U.S. Appl. No. 11/308,932.
The Response filed Oct. 9, 2009 to the Office Action mailed Jun. 30, 2009 in related U.S. Appl. No. 11/308,932.
The Response filed Feb. 4, 2010 to the Office Action mailed Jan. 5, 2010 in related U.S. Appl. No. 11/308,932.
Product Brochure—Whiteside Ortholoc Modular Knee System; Total Condylar, Dow Corning 1989 (Whitesidetotalcondylar).
Restriction Requirement mailed Mar. 23, 2009 in related U.S. Appl. No. 11/209,932.
Election filed Apr. 28, 2009 in related U.S. Appl. No. 11/209,932.
Final Office Action mailed May 7, 2010 in related U.S. Appl. No. 11/209,932.
Restriction Requirement mailed Mar. 23, 2009 in related U.S. Appl. No. 11/209,930.
Election filed Apr. 28, 2009 in related U.S. Appl. No. 11/209,930.
Office Action mailed Jun. 29, 2009 in related U.S. Appl. No. 11/209,930.
Response filed Sep. 29, 2009 in related U.S. Appl. No. 11/209,930.
Final Office Action mailed Dec. 8, 2009 in related U.S. Appl. No. 11/209,930.
Response filed May 4, 2010 in related U.S. Appl. No. 11/209,930.
The Office Action mailed Apr. 30, 2007 in related Australian application No. 2003217551.
The Office Action mailed Dec. 11, 2007 in related Australian application No. 2003217551.
The Office Action mailed Apr. 5, 2007 in related Canadian application No. 2,475,078.
The Response filed Oct. 5, 2007 to the Office Action mailed Apr. 5, 2007 in related Canadian application No. 2,475,078.
The International Search Report mailed Jul. 8, 2003 in related International Application No. PCT/US2003/04750.
The Office Action mailed Oct. 7, 2008 in related U.S. Appl. No. 11/209,933.
The Final Office Action mailed Aug. 17, 2006 in related U.S. Appl. No. 10/370,154.
The Response filed Jul. 5, 2006 to the Final Office Action mailed Aug. 17, 2006 in related U.S. Appl. No. 10/370,154.
The Office Action mailed Feb. 17, 2006 in related U.S. Appl. No. 10/370,154.
The Response and RCE filed Dec. 16, 2005 to the Office Action mailed Feb. 17, 2006 in related U.S. Appl. No. 10/370,154.
The Advisory Action mailed Nov. 29, 2005 in related U.S. Appl. No. 10/370,154.

The Response filed Nov. 4, 2005 to the Final Office Action mailed Aug. 5, 2005 in related U.S. Appl. No. 10/370,154.
The Final Office Action mailed Aug. 5, 2005 in related U.S. Appl. No. 10/370,154.
The Response filed May 31, 2005 to the Office Action mailed Mar. 1, 2005 in related U.S. Appl. No. 10/370,154.
The Office Action mailed Mar. 1, 2005 in related U.S. Appl. No. 10/370,154.
International Preliminary Examination Report mailed Apr. 26, 2004 in related International application No. PCT/US2003/04750.
Response filed Sep. 9, 2010 in related U.S. Appl. No. 11/209,932.
The European Office Action mailed Mar. 23, 2011 in related European Patent Application No. 03713503.5.
The Translation of the Japanese Office Action of Reasons for Rejection dated Jan. 7, 2008 and dispatched on Jan. 16, 2008 in related Japanese application No. 2003-569089.
Office Action mailed Jan. 5, 2010 in U.S. Appl. No. 11/209,932.
Extended European Search Report mailed Jul. 13, 2011 in related European Patent Application No. EP11166282.1.

* cited by examiner

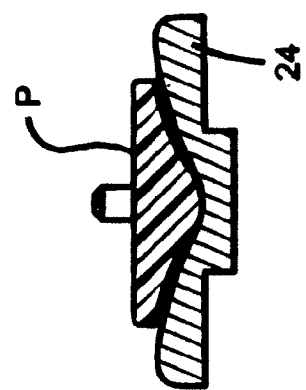
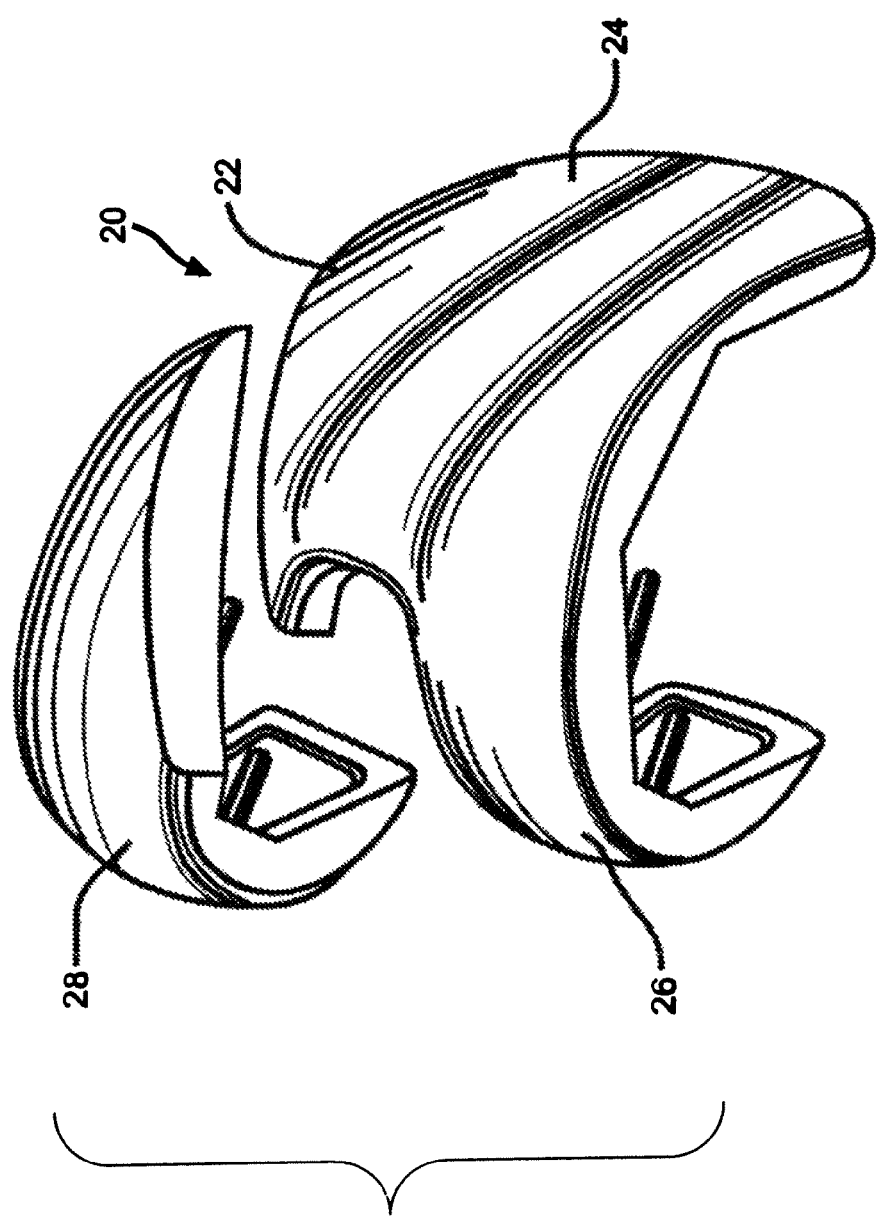

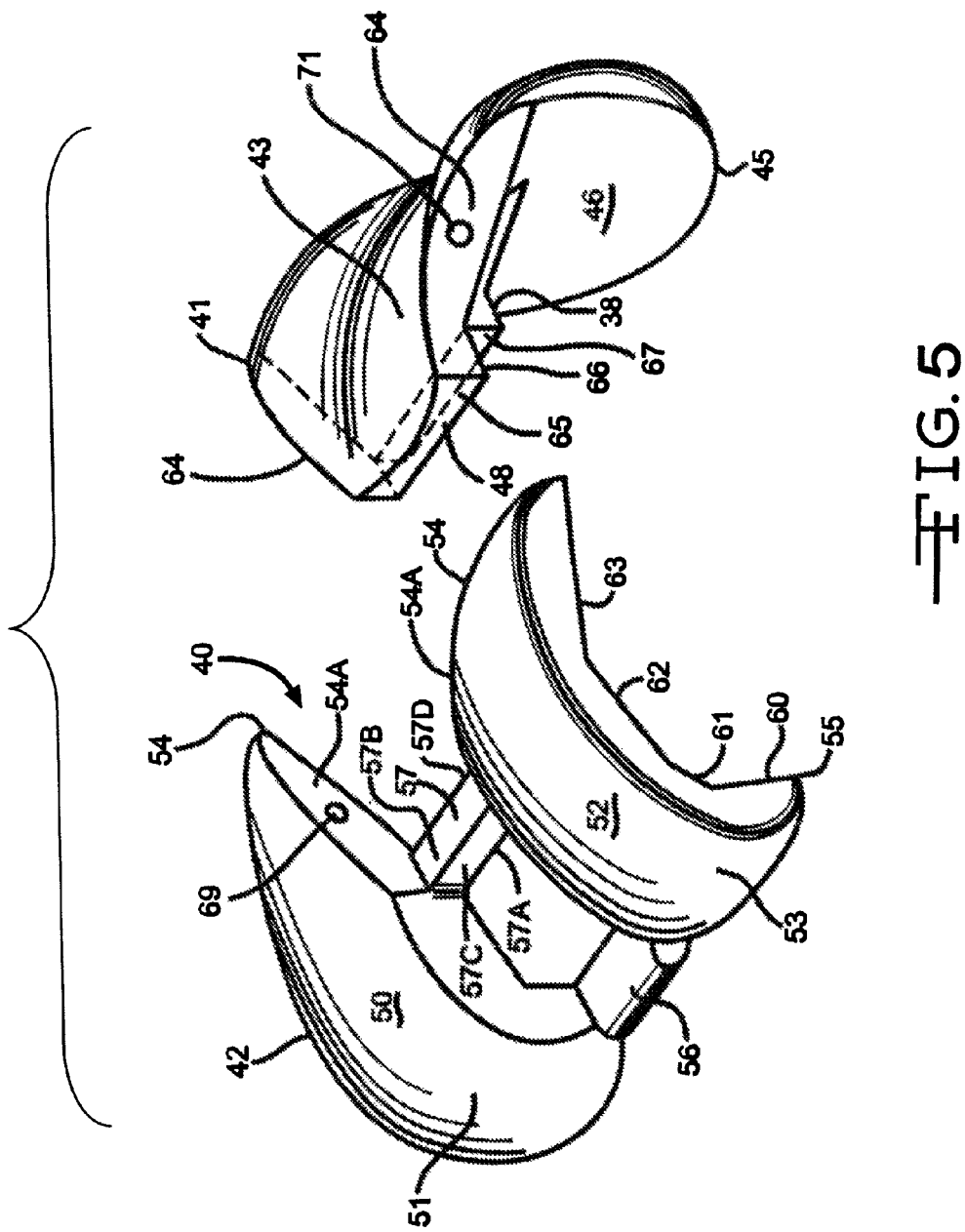

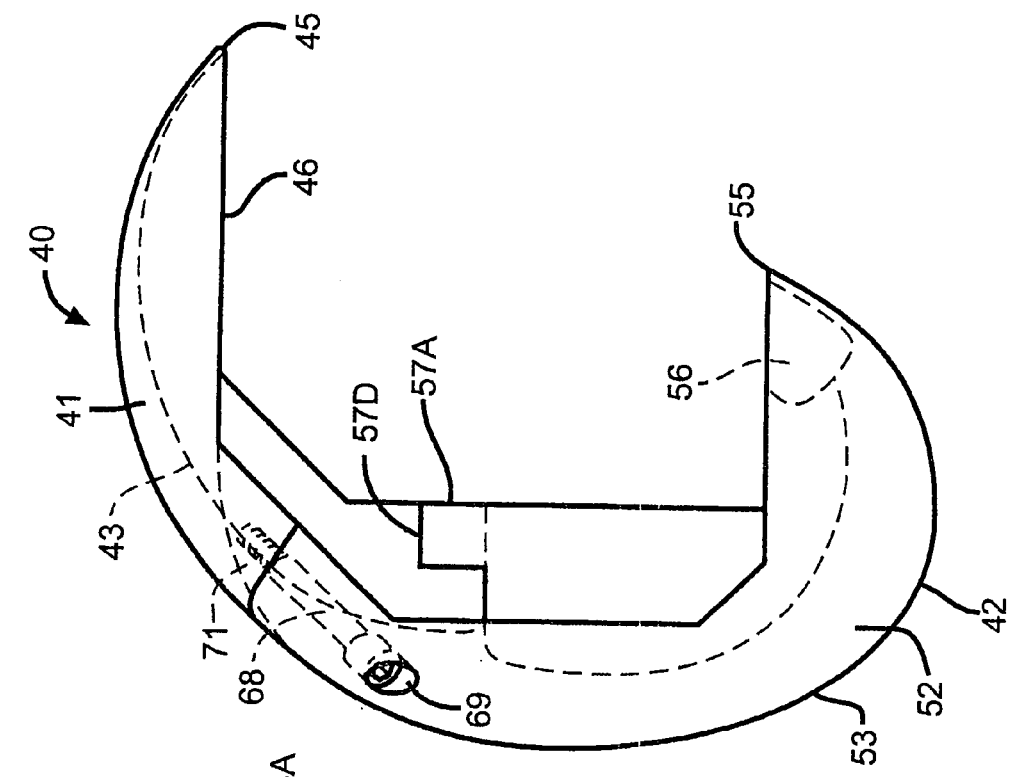
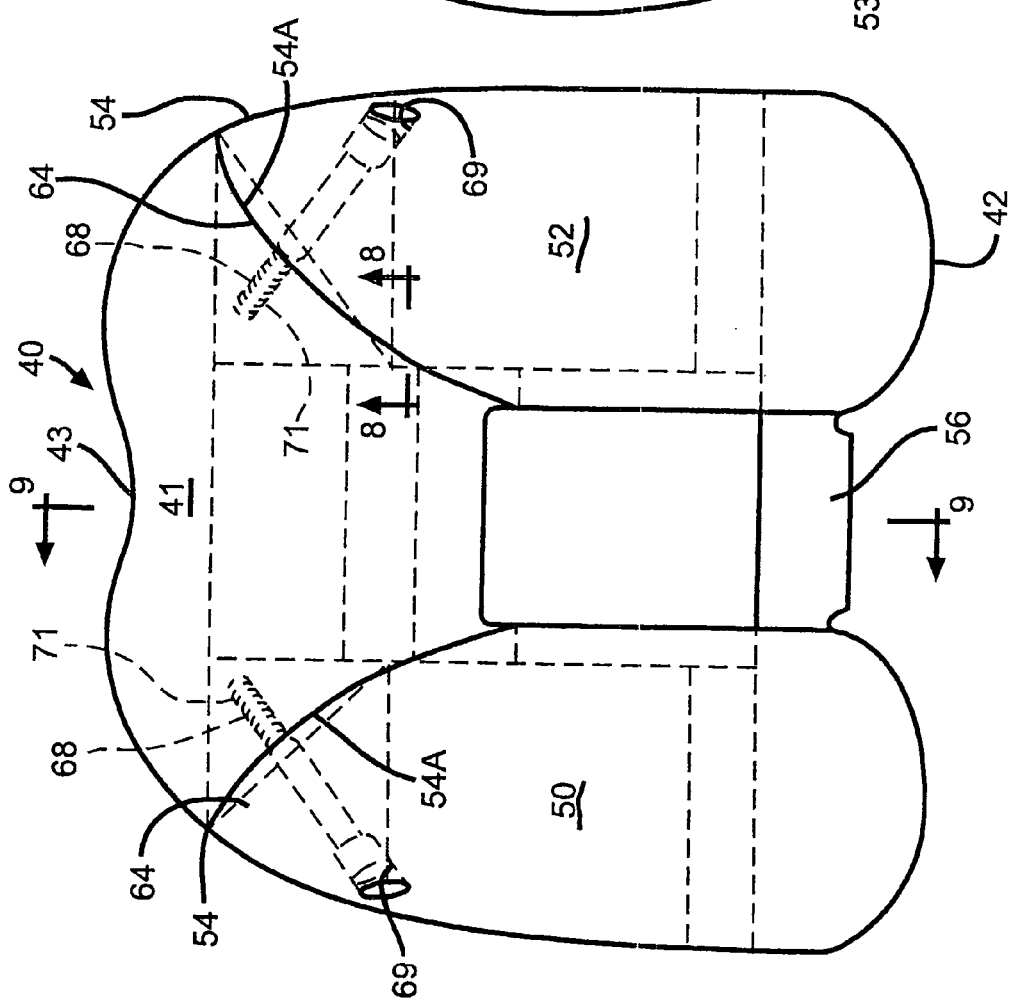

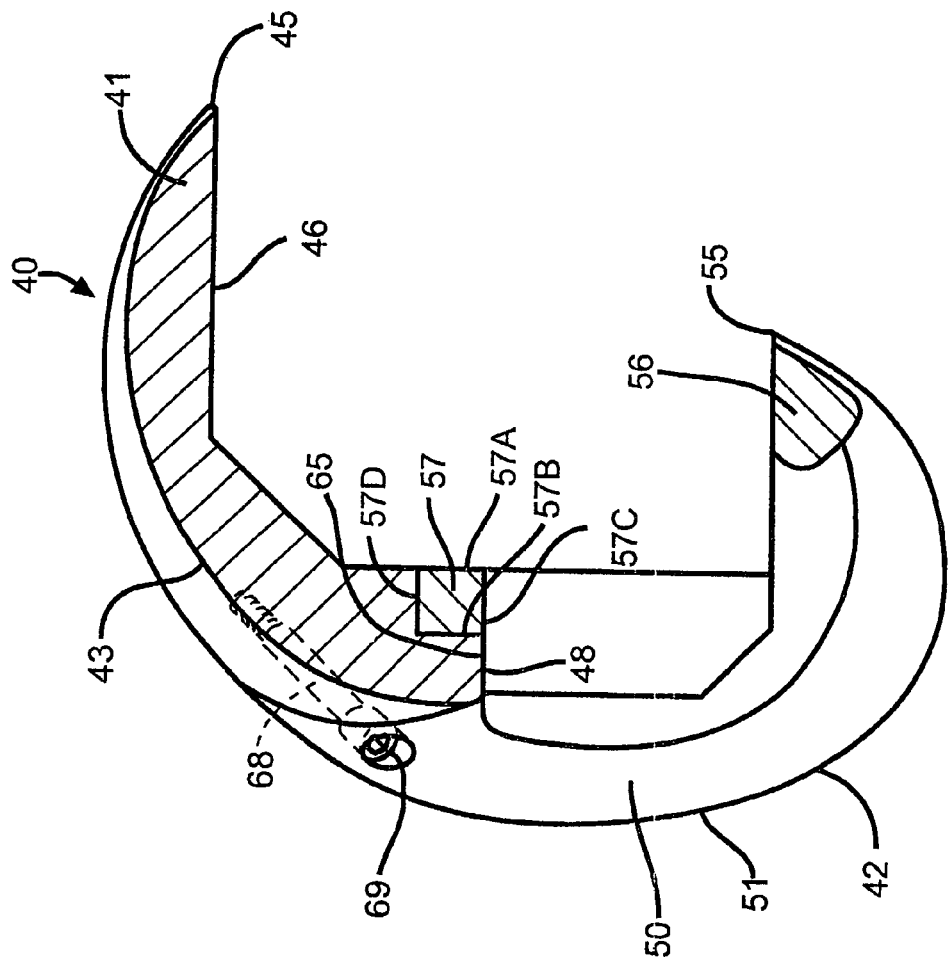
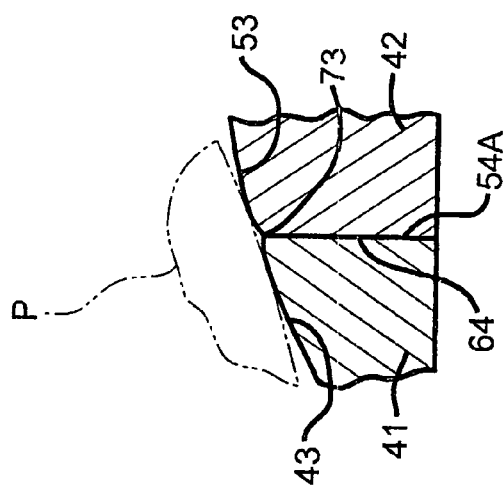
FIG. 9
FIG. 8

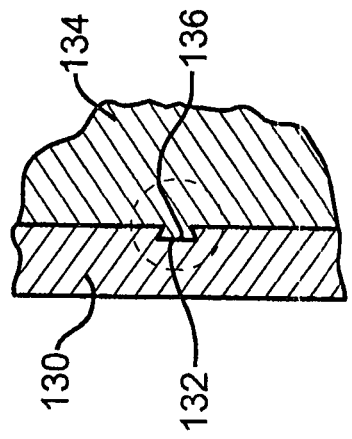
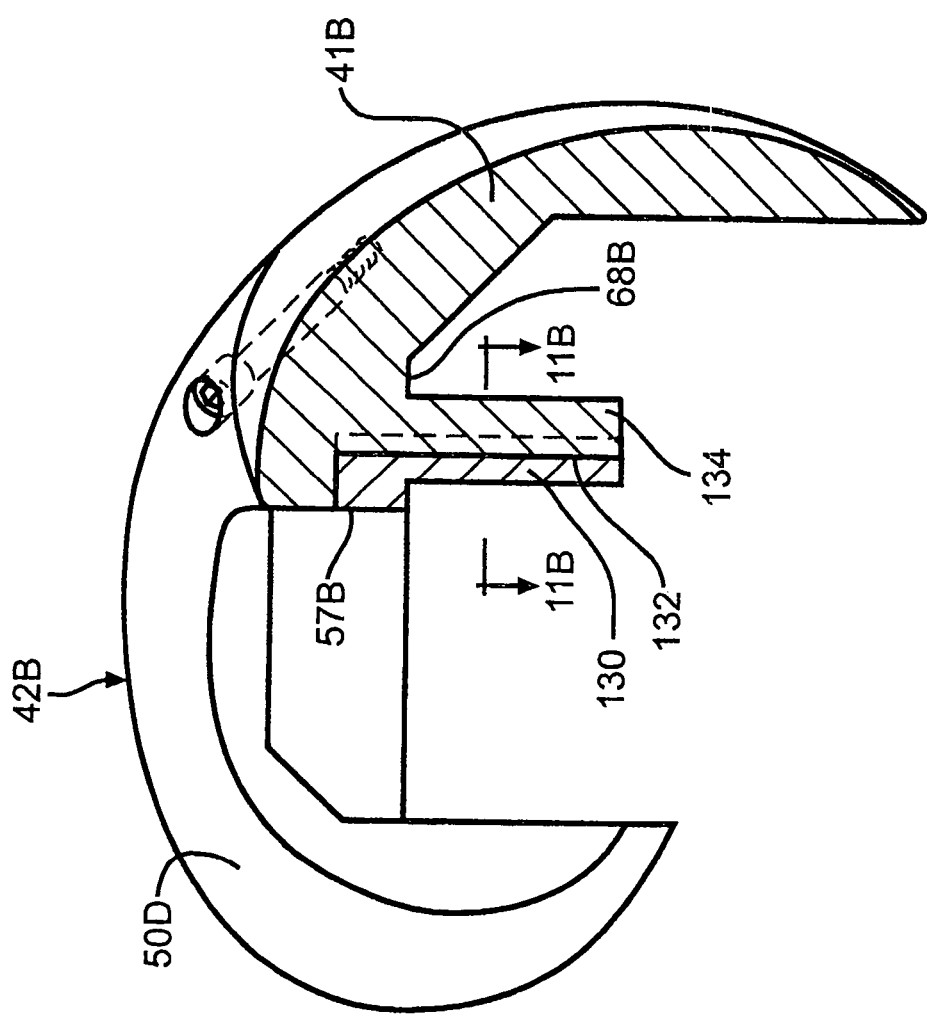

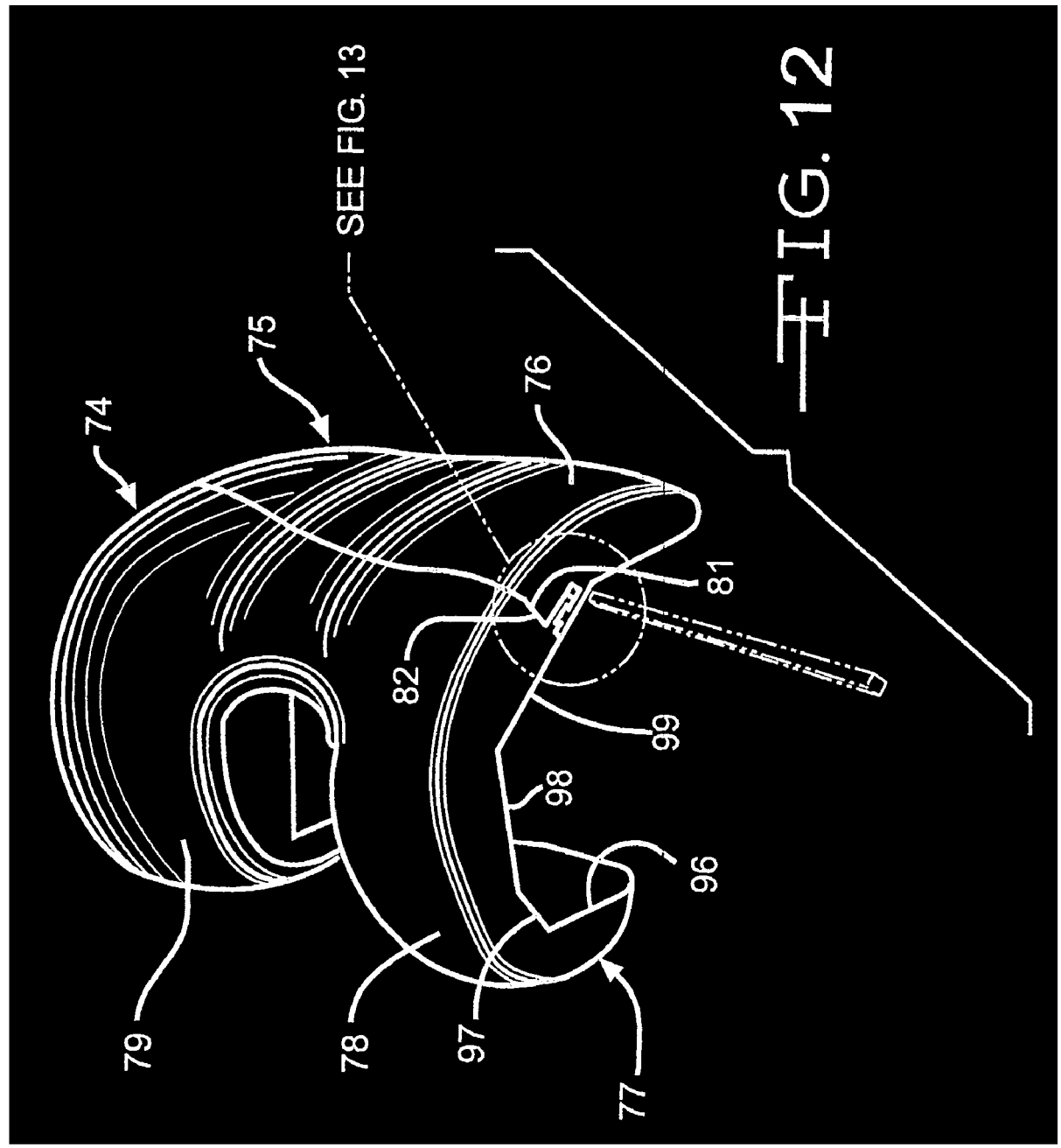

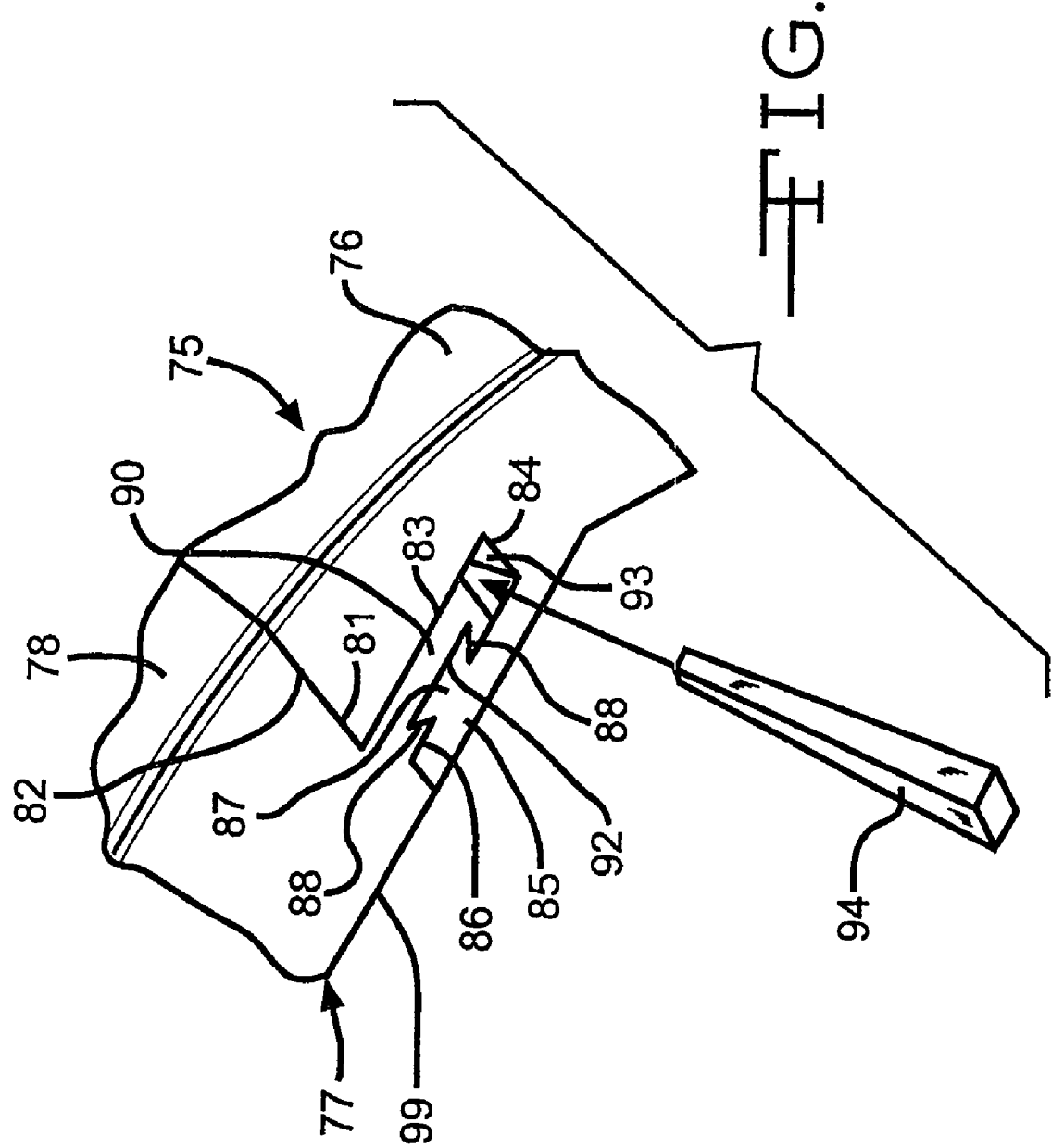

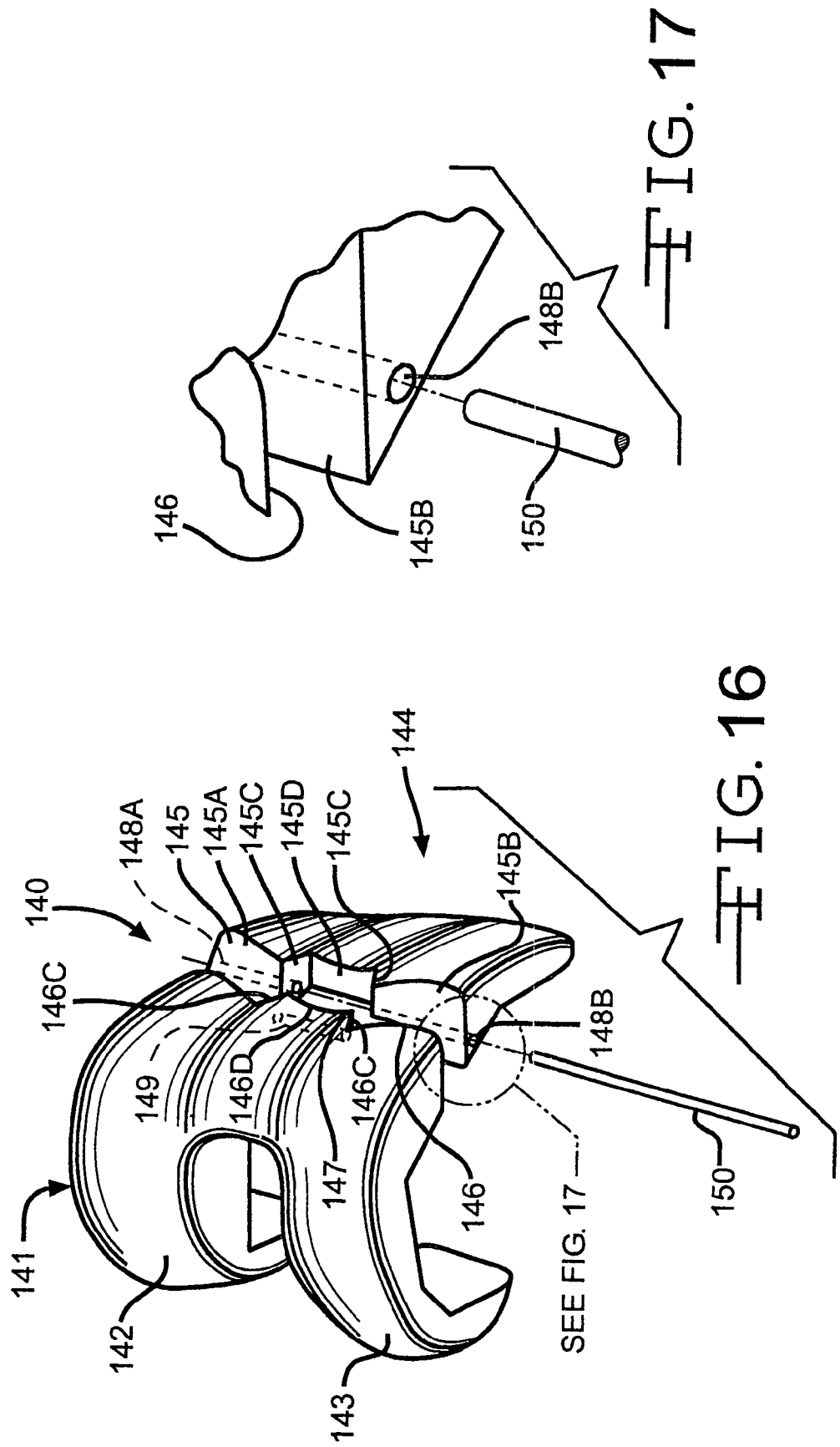

KNEE ARTHROPLASTY PROSTHESIS METHOD

CROSS REFERENCE TO RELATED APPLICATION

This patent application is a divisional of U.S. patent application Ser. No. 10/370,154, filed Feb. 19, 2003, and claims the benefit under 35 U.S.C. §119(e) of U.S. Provisional Patent Application Serial No. 60/358,174, filed Feb. 20, 2002.

BACKGROUND OF THE INVENTION

In performing knee arthroplasty with conventional knee prostheses, it has been necessary to form large incisions in order to accommodate the preparation of the femur to receive the prosthesis and to accommodate the reception of a fairly large prosthesis into the incised femur for implantation on the prepared distal end of the femur. As is appreciated by those skilled in the art, it is desirable to minimize the size of any incision as the smaller the incision, the more rapidly the patient may recover. Prior art prostheses formed with a single piece metal component having both left and right condylar portions integral with the patellar flange area require large incisions in order to accommodate implantation in the prepared femur. In contrast, under the present invention, through the use of multiple pieces for the femoral component, it is possible to greatly reduce the size of any such incision, thereby reducing the amount of damage to soft tissue from any such arthroplasty and speeding the time of recovery. Similarly, it is desirable to minimize the size of any incision in the tibia during any implantation of the tibial component.

SUMMARY OF THE INVENTION

The present invention is directed to a prosthesis for use in knee arthroplasty including total knee arthroplasty which is minimally invasive to the patient and to a method for performing surgery using such prosthesis including the femoral and tibial components thereof. Under the invention, the femoral component and, preferably, the tibial component are manufactured in at least two and possibly three or more pieces. However, it is possible that the tibial component could be a single piece, monoblock construction as well as modular multipiece construction. In both the single piece and multipiece construction, there is also provided a plastic articular surface insert piece. The pieces are designed to be assembled together following insertion into the knee. This allows total knee arthroplasty to be performed through very small incisions, as small as three inches, in each of the distal end of the femur and proximal end of the tibia. Following insertion, the pieces of the femoral component implanted at the distal end of the femur are joined together with a locking mechanism to form the modular femoral component and the pieces of the tibial component implanted at the proximal end of the tibia are assembled to form the modular tibial component.

Femoral Component

The femoral component may have three component pieces for a cruciate retaining design and two component pieces for a cruciate sacrificing design. It may be manufactured as two or three separate pieces or manufactured as a single unitary member which is subsequently cut or otherwise divided into two or three separate pieces. The pieces are provided with a locking joint for retaining the pieces together following insertion in distal end of the femur. The locking joint for the pieces is placed at the area of low patella/femoral contact, a low stress area of the femur. This corresponds to the anterior chamfer cut of a routine total knee arthroplasty and the area can be easily reinforced to accommodate the additional thickness of the locking joint. Various locking mechanisms may be employed for joining the pieces together including screws or a transverse locking pin which may be inserted from the medial side and/or lateral side. The locking mechanisms of whatever type lock the component pieces together into a solid assembled prosthesis. The prosthesis will be additionally reinforced by the underlying bone and/or cement fixation and will produce a durable construction. The patellar flange and the area of any joint between assembled components which may be contacted by the patella should be smoothed and, possibly, recessed to prevent premature wear of the patellar member as it tracks over the joint in the femoral component.

Tibial Component

The tibial component preferably has two pieces, namely, a tibial base and a tibial stem. It is also inserted in pieces from the side. It may also be a monoblock, one-piece tibial component with pegged or short stem fixation. The tibial base may have of a flat baseplate with anterior and posterior dovetails and may have a tapered transverse keel. The other piece of the tibial component is a modular stem which is inserted from the top after the baseplate is inserted. This design allows the components to be inserted through the minimal incision and still have long term stability. The stem is preferably fixed with a reverse Morse taper so that it can be driven through the baseplate like a spike.

Patellar Component

A standard conforming dome configuration patellar component is Utilized, with the main difference being its method of insertion. It may be inserted without everting the patella. This is accomplished with the use of special instrumentation.

BRIEF DESCRIPTION OF THE DRAWINGS

FIG. 2 is a perspective view of a second embodiment of femoral component showing the lateral condyle as a separate piece from the remainder of the femoral component.

FIG. 2A is a sectional view showing a patellar member engaged to the articulating surface of the patellar femoral flange piece.

FIG. 5 is a perspective view of an embodiment of femoral component showing the patellar femoral flange piece as a separate piece from the remainder of the femoral component.

FIG. 6 is a front view of the embodiment of the femoral component of FIG. 5.

FIG. 7 is a side view of the embodiment of the femoral component of FIG. 5.

FIG. 8 is a sectional view taken through line 8-8 of FIG. 6.

FIG. 9 is a sectional view taken through line 9-9 of FIG. 6.

FIG. 11A is a view similar to FIG. 9 for the embodiment of FIG. 11.

FIG. 11B is a sectional view through line 11B-11B of FIG. 11A.

FIG. 12 is a perspective view of another embodiment of femoral component showing the patellar femoral flange piece as a separate piece from the remainder of the femoral component and showing one form of design for connecting the patellar femoral flange piece to the remainder of the femoral component.

FIG. 13 is an enlarged view of the circled portion of FIG. 12.

FIG. 16 is a perspective view of another embodiment of femoral component showing the patellar femoral flange piece as a separate piece from the remainder of the femoral component.

FIG. 17 is an enlarged view of the circled portion of FIG. 16.

DETAILED DESCRIPTION OF THE PREFERRED EMBODIMENT

Figure 1:
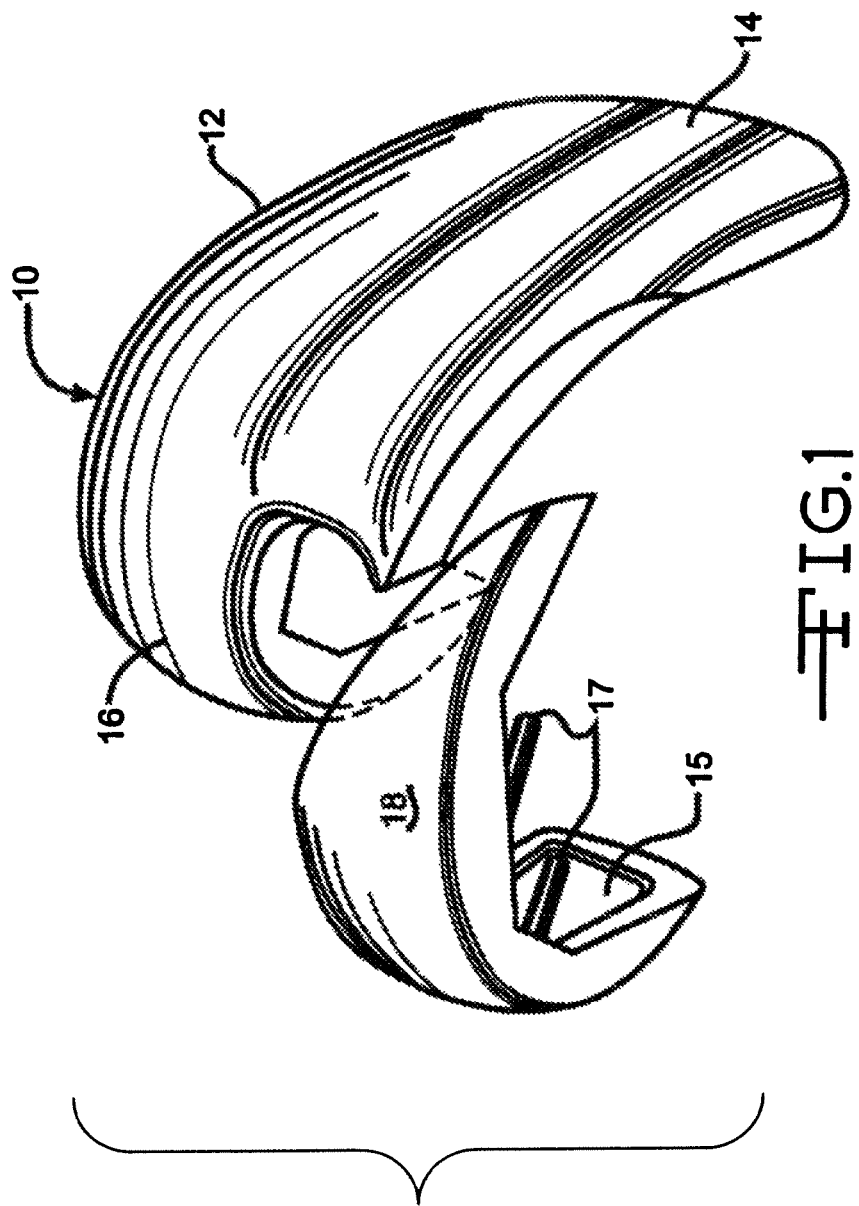
FIG. 1 is a perspective view of one embodiment of femoral component showing the medial condyle as a separate piece from the remainder of the femoral component.

Referring to FIG. 1, there is shown one embodiment of femoral component generally designated by the numeral 10. The femoral component includes a first piece 12 having a patellar flange portion 14 and an integral, unitary lateral condyle portion 16 extending therefrom. A prior art femoral component would also have an integral, unitary medial condyle on the opposite side from the lateral condyle portion 16. Under the present invention, there is provided, as a separate piece, a medial condyle piece 18 intended to be assembled to the first piece 12 following implantation of both the first piece 12 and the medial condyle piece 18 in the patient. The assembly mechanism or locking joint for securing the medial condyle piece 18 to the first piece 12 will be hereinafter described.

As shown in FIG. 1, the medial condyle piece 18 is provided with a recess 15 for receiving bone cement and a pair of fixation pins 17. The first piece 12 may also be provided with one or more recesses and fixation pins. If it is desired to have a prosthesis for implantation without bone cement, the recesses such as the recess 15 can be replaced by one of several types of porous surfaces well known in the art for bone in-growth.

Referring to FIG. 2, there is shown a second embodiment of a femoral component 20 having a first piece 22 with a patellar femoral flange portion 24 and an integral, unitary medial condyle portion 26. The second component of this embodiment is a lateral condyle piece 28 which may be joined with the first piece 22 following implantation of both the first piece 22 and the lateral condyle piece 28 in the femur of the patient.

FIG. 2A shows a sectional view of patellar member P in contact with the articulating surface of the patellar femoral flange portion 24.

Figure 3:
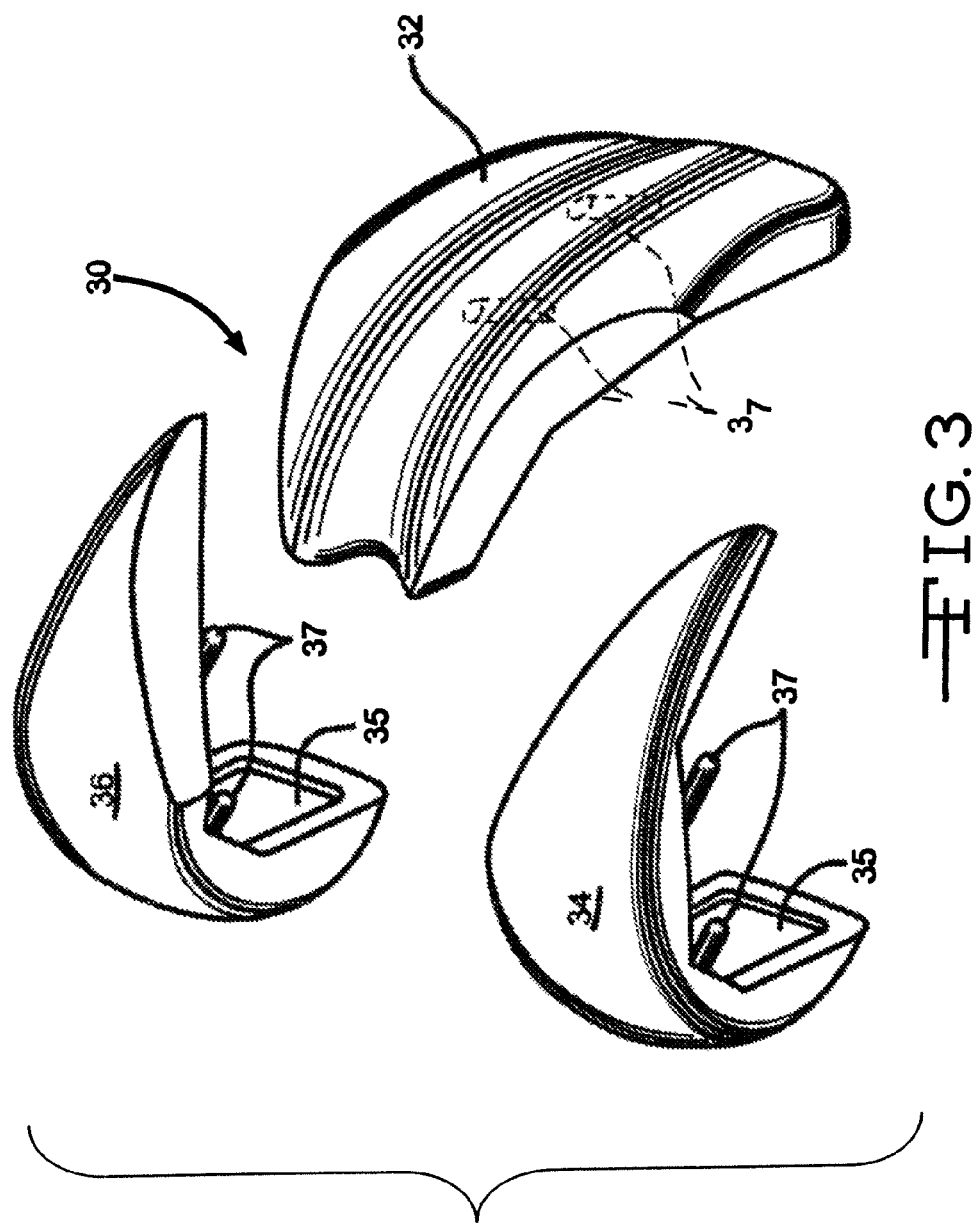
FIG. 3 is a perspective view of another embodiment of femoral component showing both the medial condyle and the lateral condyle as separate pieces from the patellar femoral flange piece of the femoral component.

FIG. 3 shows yet another embodiment of a three-piece femoral component 30. Under this embodiment, there is provided a patellar femoral flange piece 32, a second piece 34 which is a medial condyle piece and a third piece 36 which is a lateral condyle piece assuming, of course, implantation in the right knee of a patient. If the femoral component 30 were implanted in the left knee of a patient, the second piece 34 would be the lateral condyle piece and the third piece 36 would be the medial condyle piece. Each of the second piece 34 and the third piece 36 are joined to the patellar femoral flange piece 32 following insertion in the patient's femur by use of a locking joint to be hereinafter described.

All three of the pieces of the femoral component may be provided with fixation pins 37 and recesses 35 if intended for use with bone cement or a porous surface if intended for non-cemented implantation.

Figure 4:
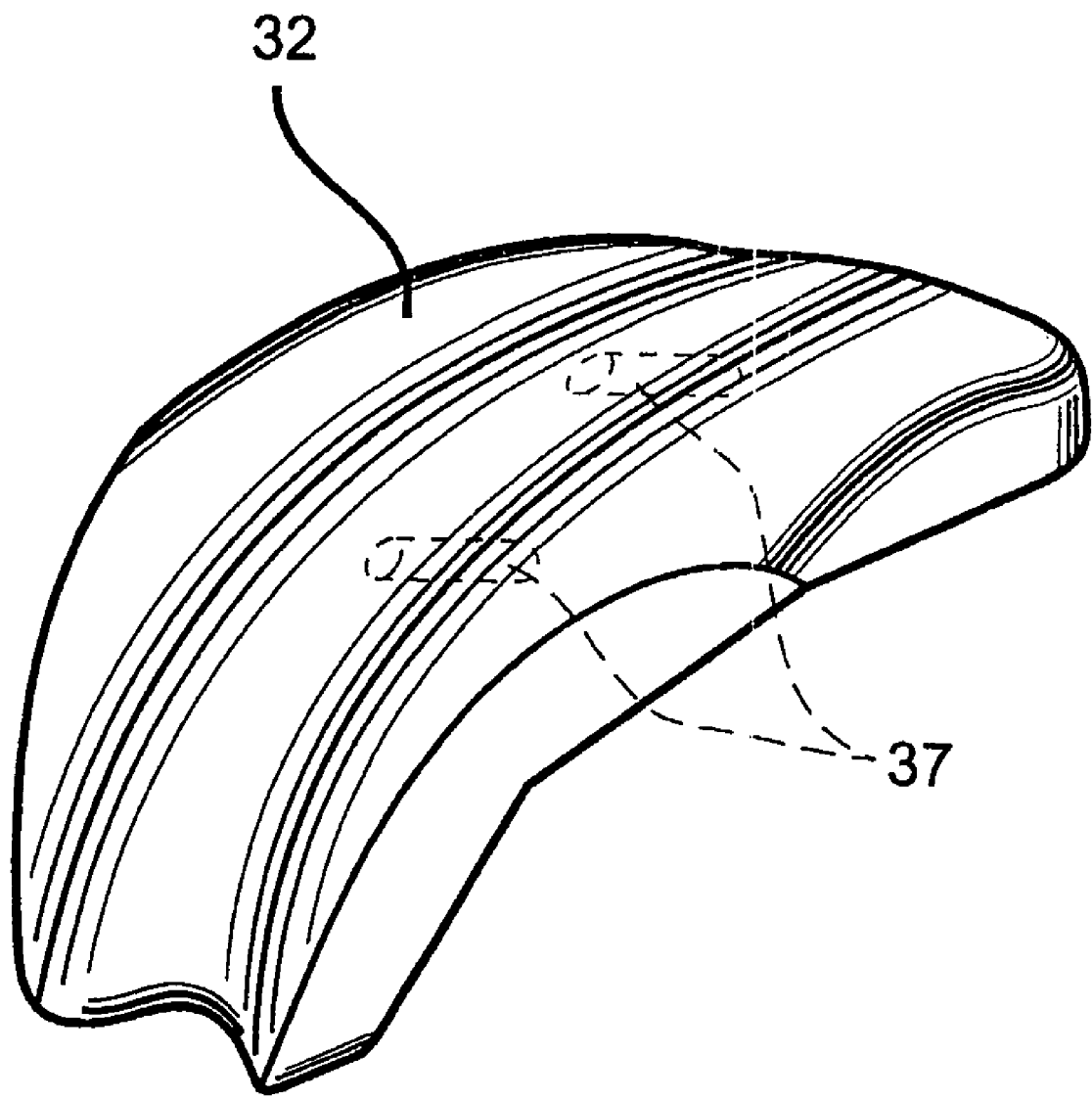
FIG. 4 is a perspective view showing the patellar femoral flange piece of FIG. 3 taken from a different angle.

FIG. 4 is a perspective view of the patellar femoral flange piece of FIG. 3 taken from a different angle.

The femoral components 10, 20 and 30 of FIGS. 1 through 3 could be used for implantation in either knee. The foregoing description for each of the femoral components 10, 20 and 30 is based on the assumption of implantation in the right knee. If they were used for implantation in the left knee, the pieces identified by the numerals 18 and 34 would be lateral condyle pieces, the pieces identified by the numerals 28 and 36 would be medial condyle pieces, the portion identified by the numeral 16 would be a medial condyle portion and the portion identified by the numeral 26 would be a lateral condyle portion.

Referring to FIGS. 5, 6, 7, 8 and 9, there is shown an embodiment of femoral component 40 having two pieces, namely, a patellar femoral flange piece 41 and a condylar piece 42. The patellar femoral flange piece 41 has a patellar engaging surface 43 shaped to allow anatomical tracking of a natural or prosthetic patella P. As shown in FIG. 5, the patellar femoral flange piece 41 has a superior bone engaging surface 46 and a patellar engaging surface 43 defining a portion of an inferior articulating surface. The patellar femoral flange piece 41 extends from an inferior end 45 to a leading end 48 which is contoured to engage the condylar piece 42. The condylar piece 42 includes a first condylar portion 50 and a second condylar portion 52 and extends from an engagement end 54 contoured to receive the leading end 48 of the patellar flange 41 to a posterior end 55. As will be appreciated by those skilled in the art, the femoral component 40 could be used for implantation in either a right knee or left knee and the first and 'second condylar portions will be either lateral or medial facing depending upon the knee in which the femoral component 40 is implanted.

The condylar piece 42 has a superior bone engaging surface with a series of bone engaging flats 60, 61, 62 and 63 disposed at varying angles consistent with cuts made in preparing the distal end of the femur to receive the condylar piece 42. If desired, the superior bone engaging surface 46 of the patellar flange piece 41 and the superior bone engaging surfaces 60, 61, 62 and 63 of the condylar piece 42 may be formed with recesses for receiving bone cement or porous surfaces for bone ingrowth and may also be provided with fixation pins.

The condylar piece 42 in the embodiment of FIGS. 5-9 is formed as a single unitary piece for implantation. As such, the first condylar portion 50 and the second condylar portion 52 are joined together with a posterior cam 56 which may be formed integral with or welded or otherwise joined to the first and second condylar portions 50, 52. The engagement end 54 of the condylar piece 42 also has the first and second condylar portions 50, 52 joined together by a laterally extending cross member 57. As will be appreciated by those skilled in the art, the use of the posterior cam 56 will result in sacrificing of the posterior cruciate ligament. As will be appreciated, in those cases where it may be necessary to sacrifice the posterior cruciate ligament for other reasons, the feature of having both a posterior cam 56 and a cross member 57 for joining the first and second condylar pieces 50, 52 will provide great rigidity to the condylar piece 42.

As can be seen in FIGS. 5, 7 and 9, the cross member 57 has a superior bone engaging surface 57A and a medial surface 57B approximately midway between the superior bone engaging surface 57A and the articulating surfaces 51 and 53 of the first condylar portion 50 and second condylar portion 52, respectively. On the posterior side of the cross member 57 is a posterior wall surface 57C extending between the superior bone engaging surface 57A and the surface 57B. Opposite the posterior surface 57C is a fourth surface 57D which will engage a corresponding surface to be described of the patellar femoral flange piece 41.

The engagement ends 54 for each of the first and second condylar portions 50, 52 each follows a curved path defined by sidewall engagement surface 54A as shown in FIGS. 5 and 6. Each of the curved engagement wall surfaces 54A extends to the general area defined by the posterior wall surface 57C of cross member 57. (See FIG. 5). The positioning of the joint defined by the surfaces 54A of the condylar piece 42 and the mating surfaces of the patellar femoral flange piece 41 is important and should be in the vicinity of the normal femoral tide mark which is a low stress area of contact by sliding engagement of the patella. By providing the joint in this area, the prosthesis has great ability to function as desired with no separation of the patellar femoral flange piece 41 from the condylar piece 42 following implantation. The normal femoral tide mark corresponds to the area of the inferior chamfer cut of a routine total knee arthroplasty.

The patellar femoral flange piece leading end 48 has a pair of curved engagement surfaces 64 following a contour for mating engagement with the respective surfaces 54A of the condylar piece 42. Centrally positioned between the curved engagement surfaces 64 is a central wall surface 65 which, when the patellar femoral flange piece 41 is engaged to the condylar piece 42, lies in substantially the same plane as the surface 57C of cross member 57. (See FIG. 9). The central wall surface 65 extends superiorly from the patellar engaging surface 43 to a ledge 66 intended to rest upon the surface 57B of cross member 57. The ledge 66 extends away from the central wall surface 65 to a central engagement surface 67 which is intended to engage the surface 57D of cross member 57. A bone engaging surface 68 extends from the central engagement surface 67 toward the anterior end 45.

As shown in FIGS. 6, 7 and 9, the condylar piece 42 may be secured to the patellar femoral flange piece 41 by means of screws 68 extending through apertures 69 extending through engagement end area 54 of the respective first and second condylar portions 50 and 52, through the engagement end surfaces 54A and into aligned threaded apertures 71 extending inwardly from the curved engagement surfaces 64 of the patellar femoral flange piece 41.

Referring to FIG. 8, there is shown the articulating surface defined by the patellar engaging surface 43 of the patellar femoral flange piece 41 and the articulating surface 59 of the condylar piece 42 in the area of the joint defined by the mating surface 54A of the condylar piece 42 and surface 64 of the patellar femoral flange piece 41. As can be seen in FIG. 8, the respective surfaces 43 and 59 are recessed slightly at such joint to provide a slight dip 73 so that any movement of the patellar member P over such joint will leave a slight gap between the surface of the patellar member P and the surfaces 43 and 59 at the dip 73.

The presence of the gap and the dip 73 has a two-fold advantage. It reduces the amount of stress in that area of the joint defined by the mating surfaces 54A and 64 at the surfaces 43 and 59. Additionally, if there is a slight mismating of the patellar femoral flange piece 41 relative to the condylar piece 42 such that one of the surfaces 43 or 59 were slightly high or lower than intended for precise fixation, the presence of the dip 73 will serve to prevent the patellar member P from contacting and being subjected to premature wear by a sharp corner of the higher piece.

Figure 10:
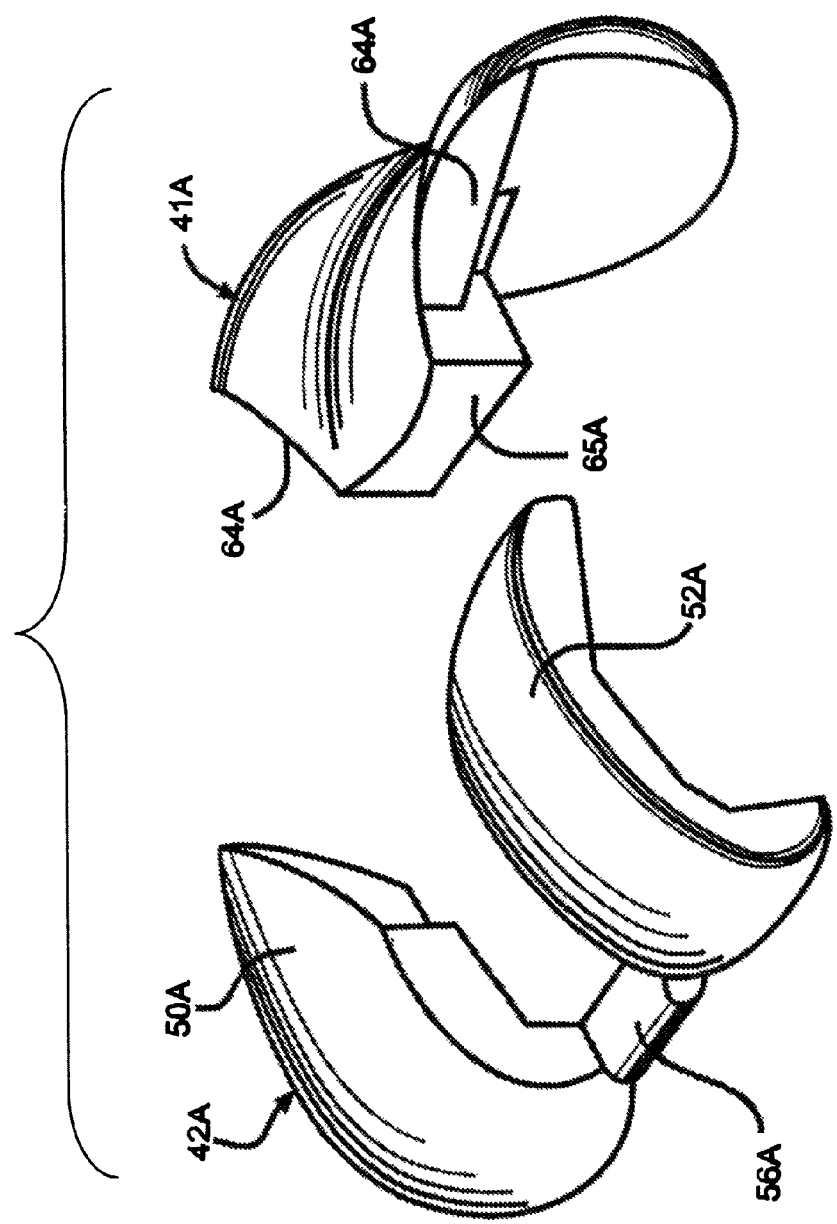
FIGS. 10 and 11 are perspective views of other embodiments of the femoral component showing the patellar femoral flange piece as a separate piece from the remainder of the femoral component.

Referring to FIG. 10, there is shown a further embodiment similar to that of FIGS. 5 through 9 but one in which there is provided a condylar piece 42A having the first condylar portion 50A is joined to the second condylar portion 52A only by a posterior cam 56A. Under this embodiment, the patellar femoral flange piece 41A has a central wall surface 65A centrally positioned between curved engagement surfaces 64A. The central wall surface 65A extends throughout the thickness of the patellar femoral flange piece 41A. Therefore, there is no ledge similar to the ledge 66 shown in FIG. 5. All other features of the embodiment of FIG. 10 are similar to corresponding features of the embodiment of FIGS. 5, 6, 7, 8 and 9.

Figure 11:
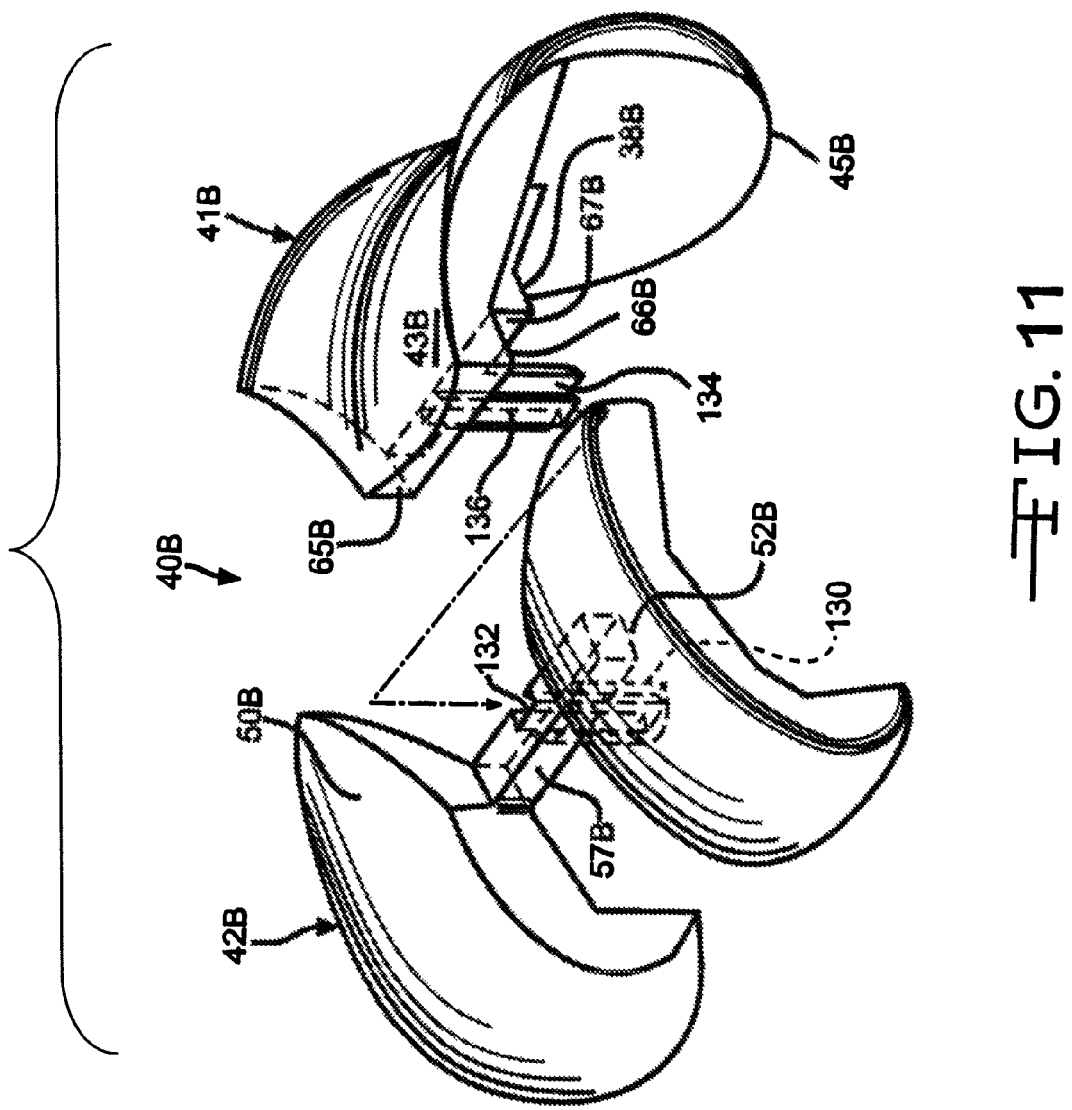

Referring to FIGS. 11, 11A and 11B, there is shown a further embodiment of femoral component 40B similar to that of FIGS. 5 through 9 but one in which there is provided a condylar piece 42B having the first condylar portion 50B joined to the second condylar portion 52B only by a cross member 57B and a modified connector means for fastening the condylar piece 42B to the patellar femoral flange piece 41 B.

The cross member 57B is provided with an extension 130 extending superiorly (i.e., downwardly as viewed in FIGS. 11 and 11A) from the cross member 57B. Both the cross member 57B and the extension 130 are provided with a common dovetail slot 132. The extension 130 is an integral unitary part of the cross member 57B and, in cross section, has a generally semicircular cross sectional configuration with the side facing the patellar femoral flange piece 41 B having a pair of flat faces on opposite sides of the dovetail slot 132.

The patellar femoral flange piece 41 B, has a configuration similar to that of the patellar femoral flange piece 41 as shown in FIG. 5, including a central wall surface 65B extending from a patellar engaging surface 43B, a ledge 66B and a central engagement surface 67B. A bone engaging surface 68B extends from the central engagement surface 67B toward the anterior end 45B. Extending superiorly from the bone engaging surface 68B is an extension 134 having a dovetail 136 sized to be snugly received in the dovetail slot 132 of the extension 130 with conforming mating surfaces. The dovetail 136 and dovetail slot 132 could have other crossectional configurations from that shown in FIGS. 11, 11A and 11B such as circular or rectangular. As will be appreciated and as can be seen from FIGS. 11A and 11B, the dovetail 136 is an integral unitary part of the extension 134; however, it extends outwardly from the surface 67B and upwardly from the surface 68B to join with surface 66B.

The respective extensions 130 of the condylar piece 42B and 134 of the patellar femoral flange piece 41B, when joined together with the dovetail 136 positioned in the dovetail slot 132 will cooperate to define a substantially cylindrical configuration; however, if desired, a different configuration, such as square, rectangular or rounded, could be utilized.

Preparatory to implantation of the condylar member 42B and patellar femoral flange piece 41B, an aperture is drilled or otherwise formed in the femur of sufficient size to receive the extensions 130 and 134.

Following positioning of the condylar piece 42B in the prepared femur with its extension 130 positioned in the prepared bone cavity, the patellar femoral flange piece 41B is moved therein, the dovetail 136 is aligned with the dovetail slot 132 and the patellar femoral flange piece 41B is moved toward the prepared femur with the dovetail 136 sliding through the dovetail slot 132 until the surface 66B of the patellar femoral flange piece 41B contacts the anterior surface of cross member 57B. Desirably, bone cement will be positioned in the prepared aperture of the femur to engage the adjoined extensions 130 and 134.

Referring to FIGS. 12 and 13, there is shown an embodiment of a two-piece femoral component 74 with a first piece 75 of a patellar flange area having a patella engagement surface 76 and a second piece 77 having a medial condyle portion 78 and a lateral condyle portion 79 formed as an integral unitary piece. The second piece 77 has a series of flats 96, 97, 98, 99 for engagement with a prepared distal end of a femur.

The first piece 75 has an abutment wall 81 extending from the patella engagement surface 76 and positioned to engage a corresponding abutment wall 82 of the second piece 77. The line of juncture between the abutment wall 81 of the first piece 75 and the abutment wall 82 of the second piece 77 is in the area of low patella/femoral contact which is a low stress area of the femur. The abutment wall 81 extends only partially through the thickness of the first piece 75. The abutment wall 81 joins with a second Wall 83 disposed substantially at right angles thereto (See FIG. 13). The second wall 83 extends to an end wall 84. Extending outwardly from the end wall 84 toward the plane defined by the abutment wall 81 is a ledge 85 having an upper surface 86 with a tongue or dovetail 87 projecting upwardly therefrom. The tongue 87 and upper surface 86 extend throughout the breadth of the first piece 75. The tongue 87 is provided with a pair of reverse taper surfaces 88 which flare outwardly from one another in a direction away from the upper surface 86.

Extending outwardly from the abutment wall 82 of the second piece 77 is an insert ledge 90 having an upper surface for mating engagement with the second wall 83 of the first piece 75. The lower portion of the insert ledge 90 opposite the upper surface has formed therein a dovetail groove 92 extending the full breadth of the second piece 77 and sized to receive the tongue 87 of the first piece 75. As can be seen from FIG. 13, when the first piece 75 and second piece 77 are joined together, there will remain a gap 93 between the end wall 84 of the first piece 75 and the end of the insert ledge 90 of the second piece 77. In order to prevent the engaged first piece 75 and second piece 77 from moving laterally relative to one another, there is provided a tapered pin 94 which may be driven into the gap 93 to function as a wedge putting the tongue 87 into compression in the dovetail groove 92 formed in the lower surface of the insert ledge 90.

Figure 15:
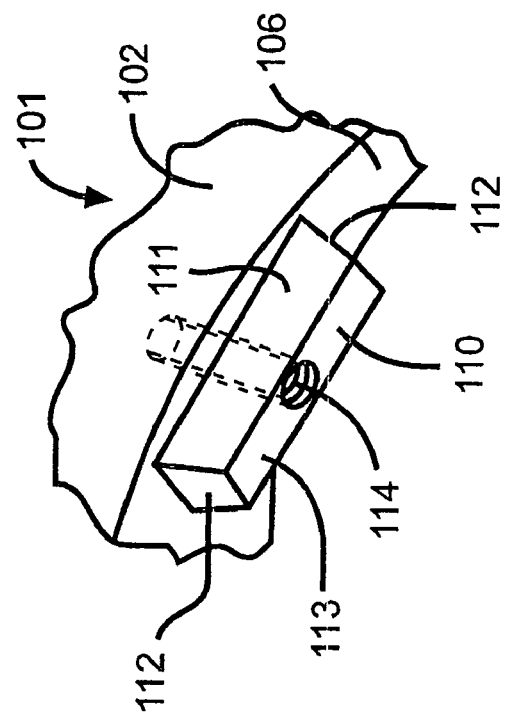
FIG. 15 is an enlarged view of the circled portion of FIG. 14.
Figure 14:
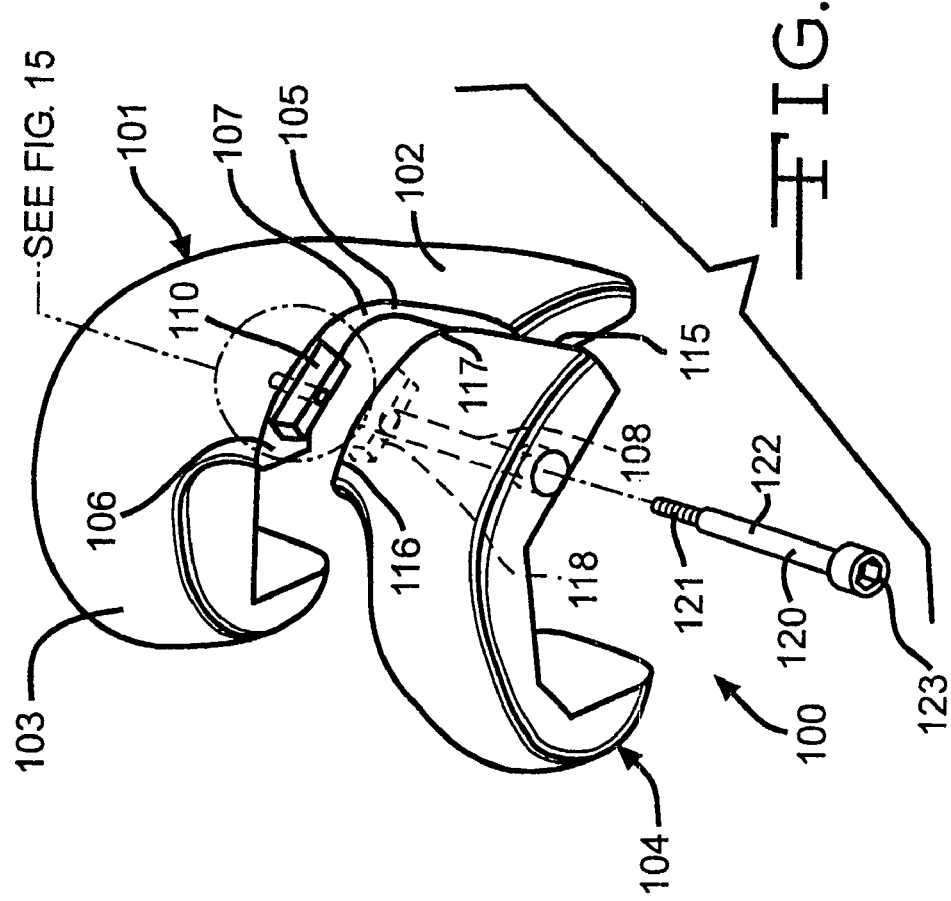
FIG. 14 is a perspective view of an embodiment of femoral component showing the lateral condyle as a separate piece from the remainder of the femoral component.

Referring to FIGS. 14 and 15, there is provided another embodiment of prosthesis. 100 with a first piece 101 having both a patellar flange area 102 and an integral, unitary lateral condyle portion 103. The prosthesis 100 also has a second piece 104 which is a medial condyle piece. The first piece 101 has a first abutment wall 105 extending generally laterally and a second abutment wall 106 extending generally longitudinally with a curved wall section 107 joining the first abutment wall 105 and the second abutment wall 106. Protruding outwardly from the second abutment wall 106 is a projection 110 having sidewalls 111 (only one of which is shown) tapering inwardly toward one another as they extend outwardly from the second abutment wall 106 and end walls 112 tapering inwardly toward one another as they extend outwardly from the second abutment wall 106. The tapering sidewalls 111 and end walls 112 are joined by an outer wall 113 substantially parallel with the second abutment wall 106. The projection 110 is integral and unitary with the remainder of the first piece 101 and may be formed by a milling process, for example. A threaded aperture 114 extends through the projection 110 from the outer wall 113 and, preferably, extends into the adjacent portion of the first piece 101.

The second piece 104 has a first abutment wall 115 positioned to engage the first abutment wall 105 of the first piece 101, a second abutment wall 116 positioned and sized to engage the second abutment wall 106 of the first piece 101 and a curved wall 117 for engagement with the curved wall 107 of the first piece 101. Formed in the second wall 116 is a recess 118 contoured to snuggly receive the projection 110 of the first piece 101. A laterally extending passageway 108 extends through the second piece 104 in alignment with the threaded aperture 114 of the first piece 101 when the second piece 104 is engaged thereto.

In order to join the second piece 104 to the first piece 101 there is provided an elongated screw 120 having a threaded section 121 for mating with the threads of the threaded aperture 114 of the first piece 101. The screw 120 has a cylindrical section 122 of larger diameter than the threaded section 121 and sized to be snugly received in the passageway 108 of the second piece. The screw 120 has an enlarged head 123 sized to fit in a countersunk area of the passageway 108 at the outer edge of the second piece 104.

Referring to FIGS. 16 and 17, there is shown a two-piece femoral component 140 including a first piece 141 having both a lateral condyle 142 and a medial condyle 143 formed as part of an integral, unitary piece. The second piece 144 defines a patellar flange area of the femoral component 140. The second piece 144 has a contoured abutment wall 145 including a first flat surface 145A extending inwardly from the lateral side, a second flat surface 145B extending inwardly from the medial side of the second piece 144 and a recess defined by first and second side walls 145C and a bottom wall 145D. The sidewalls 145C taper inwardly toward one another as they extend from their respective flat surfaces 145A and 145B to the bottom 145D. Preferably, the bottom wall 145D is curved; however, it could be flat.

The first piece 141 is provided with an abutment wall 146 having a contour to be snuggly engaged to the abutment wall 145 of the second piece 144. As such, the abutment wall 146 includes a tongue 147 contoured to fit snuggly in the groove defined by sidewalls 145C and bottom wall 145D of the second piece 144. The tongue 147 is defined by sidewalls 146C, 146C and an end wall 146D contoured to snuggly engaged the wall 145D forming the bottom of the groove of the second piece 144. The walls 146C, 146C taper inwardly toward one another as they extend toward the wall 146D and snuggly engage the tapered sidewalls 145C of the second piece 144.

The second piece 144 has formed therein a first passageway 148A which extends inwardly from the lateral edge and is substantially parallel to the first flat surface 145A and a second passageway 148B which extends inwardly from the medial edge and is substantially parallel to the second flat surface 145B. A passageway 149 is formed in the tongue 147 in a position to be aligned with the passageways 148A and 148B when the first piece 141 is engaged to the second piece 144, with the tongue 147 fitting in the groove. A pin 150 may be inserted through the passageway 148B, the passageway 149 and the passageway 148A to secure the first piece 141 to the second piece 144. The pin 150 could be cylindrical and press fit into the respective passageways 148A, 148B and 149 assuming the passageways were cylindrical or could be tapered assuming such passageways had the appropriate taper. Additionally, one of the passageways, passageway 148A, for example, could be threaded, in which case the pin 150 would have a threaded end for engagement therewith.

In each of the embodiments, the respective lines of juncture between abutting walls of the assembled pieces have been selected to be located generally in the area of the normal femoral tidemark which is a low stress area.

Figure 18:
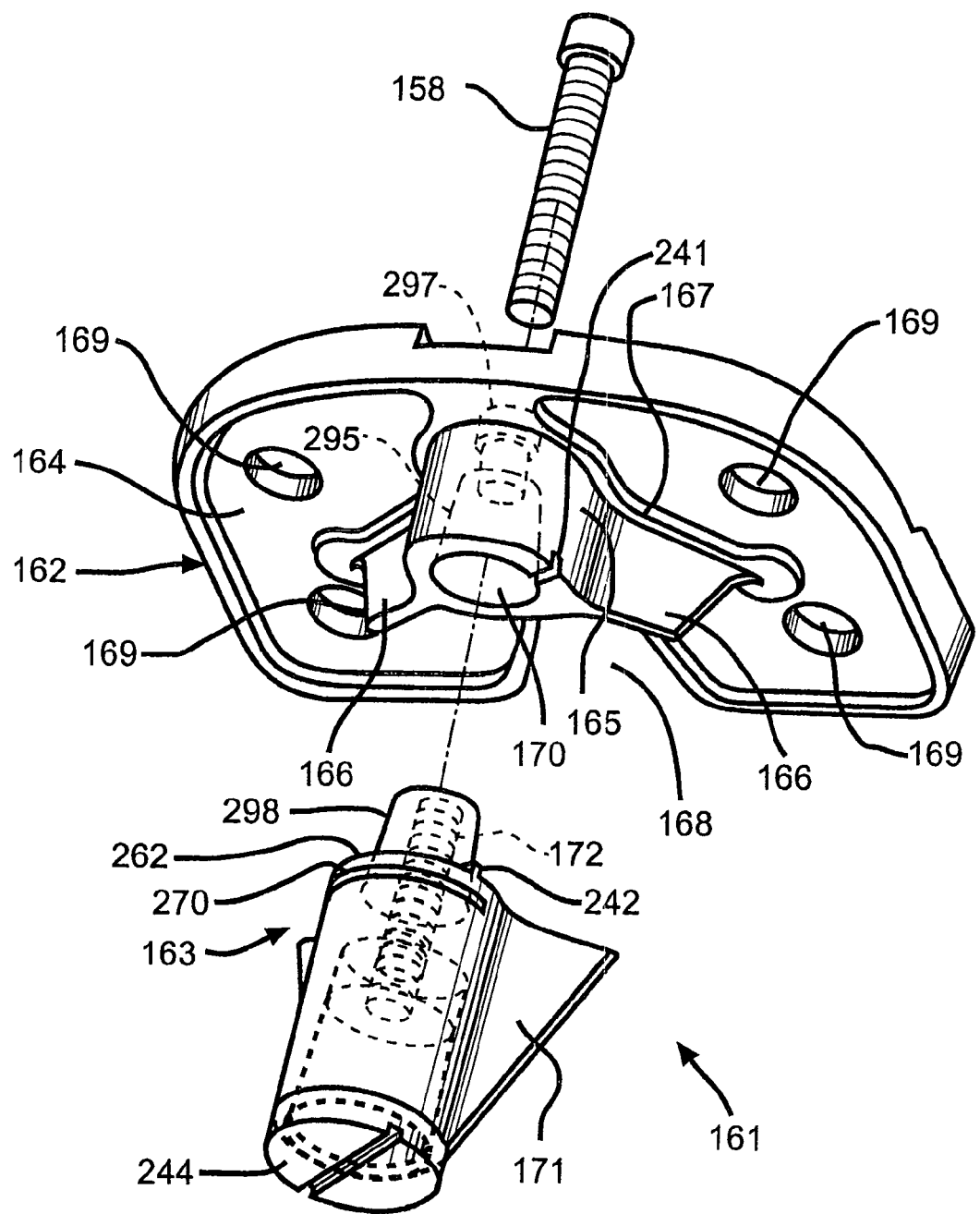
FIG. 18 is a perspective view of the tibial component showing the stem portion thereof as a separate piece from the base.

Referring now to FIG. 18, there is shown a tibial component generally designated by the numeral 161. The tibial component 161 includes a tibial base 162 and a tibial stem 163. The tibial base 162 has an inferior surface 164 intended to engage the prepared proximal end of the tibia of the patient and a superior surface (not shown) to which may be affixed a plastic insert contoured to be engaged by the condylar portions of a femoral component. The plastic insert may have one of a number of well known mechanisms for being attached to the tibial base 162 such as a dove tail locking mechanism, for example. The plastic insert may be inserted either laterally or proximally depending on the specific design of the tibial base and the condition of the patient as determined by the surgeon. Extending distally from the inferior surface 164 is a base extension 165 having a generally cylindrical shape but with a pair of fixation wings or fins 166 extending outwardly from the cylindrical portion of the base extension 165. A platform 167 is raised from the inferior surface 164 and follows a contour encircling the base extension 165 including the wings 166. The wings 166 function as fixation fins for maintaining the tibial base 162 in a fixed rotational position when implanted on the prepared proximal end of the tibia. The tibial base 162 is provided with a notch 168 to accommodate the posterior cruciate ligament and a plurality of apertures 169 for receiving screws for engagement to an augmentation block, if one is needed, or for securing the tibial base 162 to the proximal end of a prepared tibia.

The tibial base 162 has a central passageway 170 extending from the superior surface 164 and through the cylindrical portion of the base extension 165. That portion of the central passageway 170 in the base extension 165 has wall surface which flares outwardly frusto conically and defines a Morse taper cavity 295 as it approaches the end of the base extension 165. A recess defining a notch 240 is formed in the end of the base extension 165. That portion of the passageway adjacent the superior surface has a diameter sized to receive a screw 158 and a countersunk area 297 to receive the enlarged head of such screw 158.

The tibial stem 163 is provided with a pair of wings or fixation fins 171 which, when the tibial stem 163 is engaged to the extension 165, will be aligned with and forming extensions of the respective wings or fins 166 of the tibial base 162. The tibial stem 163 is provided with a Morse taper extension 298 sized to be snugly received in the Morse taper cavity 295 of the tibial base 162. A shoulder 262 extends outwardly from the Morse taper extension 298. A raised tab 242 extends proximally from the shoulder 202 and is sized to fit snugly in the notch 210 and, when so positioned, assures alignment of the fixation fins 171 of the tibial stem 163 with the fins 166 of the tibial base 162.

A threaded passageway 172 is formed in the Morse taper extension 298 and is aligned with the central passageway 170 when the tibial stem 163 is engaged to the extension 165. The tibial stem 163 is supported on the tibial base 162 by the screw 158 extending through the central passageway 170 of the tibial base 162 and engaged to the threaded passageway 172. A plug 244 is engaged in the distal end of the tibial stem 163 to prevent blood or other contaminates from entering the threaded passageway 172. The plug 244 may be secured to the tibial stem 163 by means of a threaded extension engaging the threaded passageway 172.

Figure 18A:
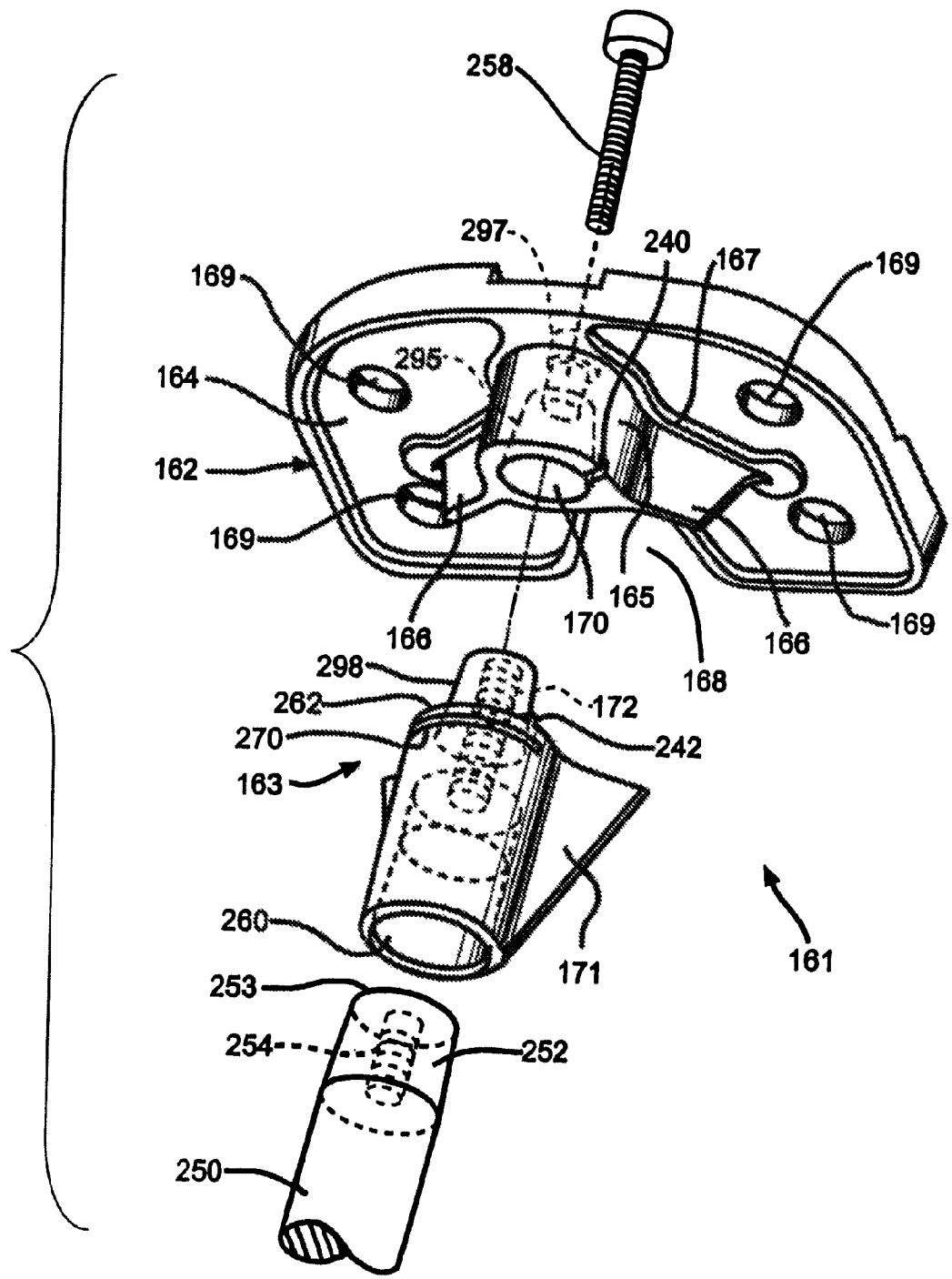
FIG. 18A is a view similar to FIG. 18 with the added feature of a stem extension as part of the tibial component.

FIG. 18A shows an embodiment similar to FIG. 18 but in which there is provided a stem extension 250 but not a plug such as the plug 244 of FIG. 18. The stem extension 250 is provided with a Morse taper 252 at its proximal end 253. A threaded recess 254 extends distally from the proximal end and has a size smaller than the threaded passageway 172. A threaded screw 258 sized to engage the threaded recess 254 secures the stem extension 250 and the tibial stem 163 to the tibial base 162. The threaded screw 258 is small enough to pass through the threaded passageway 172 without engaging its threads.

The distal end of the tibial stem 163 has a cavity 260 tapering outwardly in a distal direction and defining a Morse taper sized to snuggly receive the Morse taper 252 of the stem extension 250. Two grooves 270 are formed in the tibial stem 163, on opposite sides, distally spaced from the shoulder 262. The purpose of the grooves 270 is to permit engagement and support for the tibial stem during implantation as will be discussed hereinafter.

Figure 19:
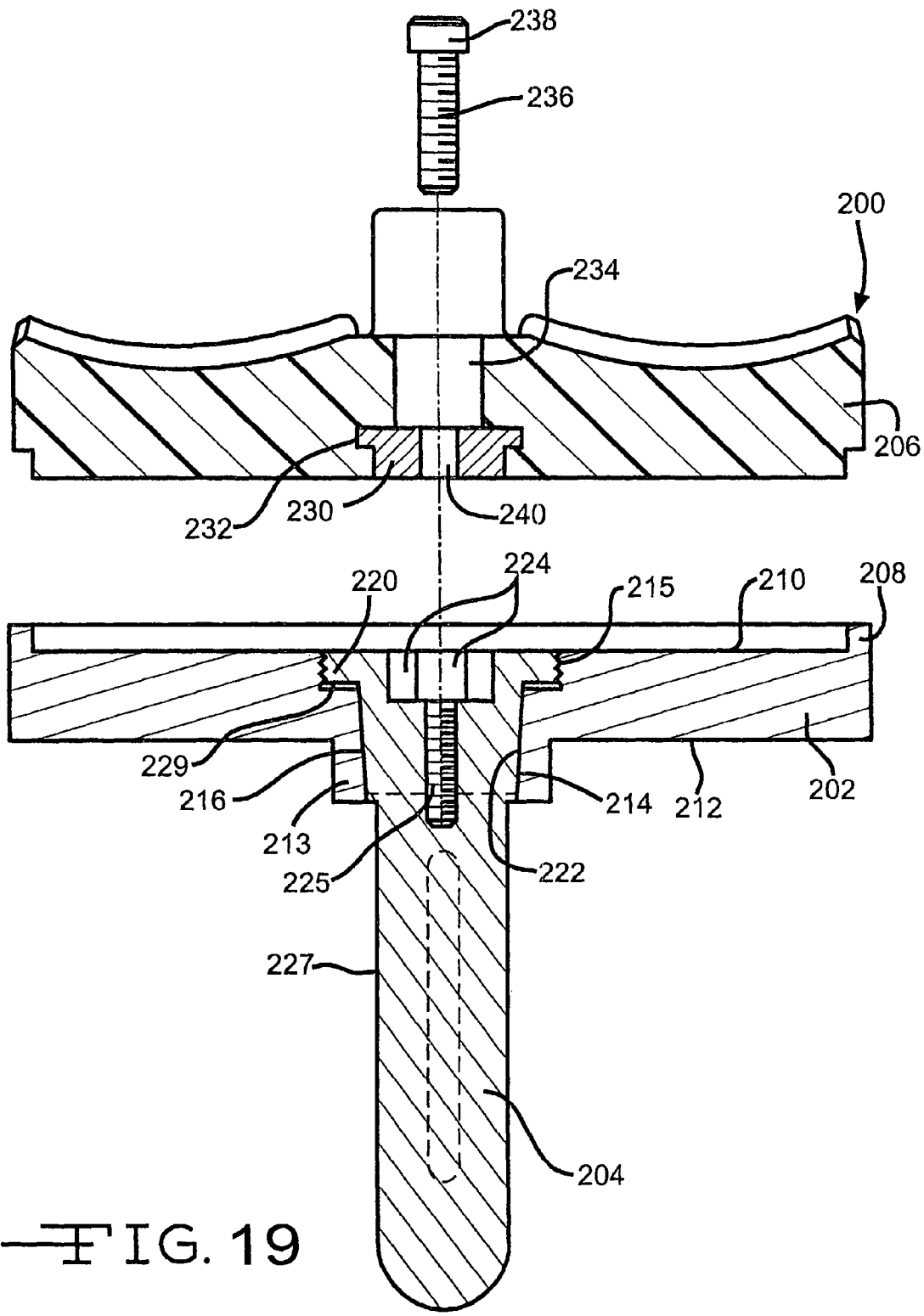
FIG. 19 is a sectional view of another, embodiment of tibial component showing the stem portion thereof as a separate piece from the base.

Referring to FIG. 19, there is a shown in section a modified embodiment of tibial component 200. Under this embodiment there is provided a tibial base 202, a tibial stem 204 and a plastic insert 206 for engagement with the tibial base 202. The tibial base, as shown in FIG. 19, has a raised wall 208 and a flat superior surface 210. The tibial base 202 has an inferior surface 212 intended to engage the prepared proximal end of the tibia of the patient. A centrally positioned short extension 213 extends from the inferior surface 212.

Extending through the tibial base 202 including the extension 213 is a passageway 214. That portion of the passageway 214 adjacent the inferior surface 210 is enlarged from the remainder of the passageway and is provided with inwardly facing threads 215 in the area adjacent the inferior surface 210. That portion of the passageway 214 extending away from the threads 215 is tapered to define a Morse taper cavity 216 throughout the remainder of the thickness of the tibial base 202 including the stem 213.

The tibial stem 204 is provided with an enlarged threaded flange 220 sized to engage the threads 215 of the tibial base 202. Extending from the flange 220 is a Morse taper extension 222 sized and contoured to be snuggly received in the Morse taper cavity 216. Extending inwardly from the inferior surface 210 is a cavity defined by a series of flats 224 which cooperate to define a hexagon or other conveniently shaped cavity for receipt of a tool for engagement therein for threading the threaded flange 220 into the threads 215.

Extending from the cavity defined by the flats 224 is a threaded aperture 225. Extending distally from the Morse taper extension 222 is a reduced size cylindrical extension 227.

The plastic insert 206 has molded therein a metal insert 230 having an enlarged flange 232 to ensure its firm engagement to the insert 206. The insert 206 is provided with a passageway 234 sized to receive a screw 236 including its enlarged head 238. The metal insert 230 is provided with a passageway 240 sized to receive the threaded portion of the screw 236 but smaller than the enlarged head 238. Following engagement of the tibial stem 204 to the tibial base 202, the plastic insert 206 is positioned on the inferior surface 210 within the upwardly extending wall 208. The screw 236 is then engaged to the threaded aperture 225 to secure the plastic insert 206 thereto.

In the surgical procedure for implanting the tibial component 200, the proximal end of the tibia is prepared by cutting a flat surface to receive the inferior surface 212 of the tibial base 202 and a cavity is drilled in the intramedullary canal of the tibia to receive the stem 204. The tibial base 202 is positioned on the prepared flat surface with the extension 213 positioned in the cavity. The tibial stem 204 is then positioned in the passageway 214 with the cylindrical extension 227 passing through the Morse taper cavity 216 and into the cavity of the intramedullary canal. Using a tool engaged to the flats 224, the stem is threadedly engaged to the threads 215 and the base 202 to cause the Morse taper extension 222 to firmly engage the Morse taper cavity 216. As may be seen in FIG. 19, the tibial stem 204 is so contoured relative to the tibial base 202, that a gap 229 will remain between the distal side of the flange 220 and the surface of the tibial base 202 extending radially outwardly from the Morse taper cavity 216. This ensures that the Morse taper extension 222 will firmly engage the Morse taper cavity 216 upon threaded engagement of the threaded flange 220 to the threads 215.

Figure 20:
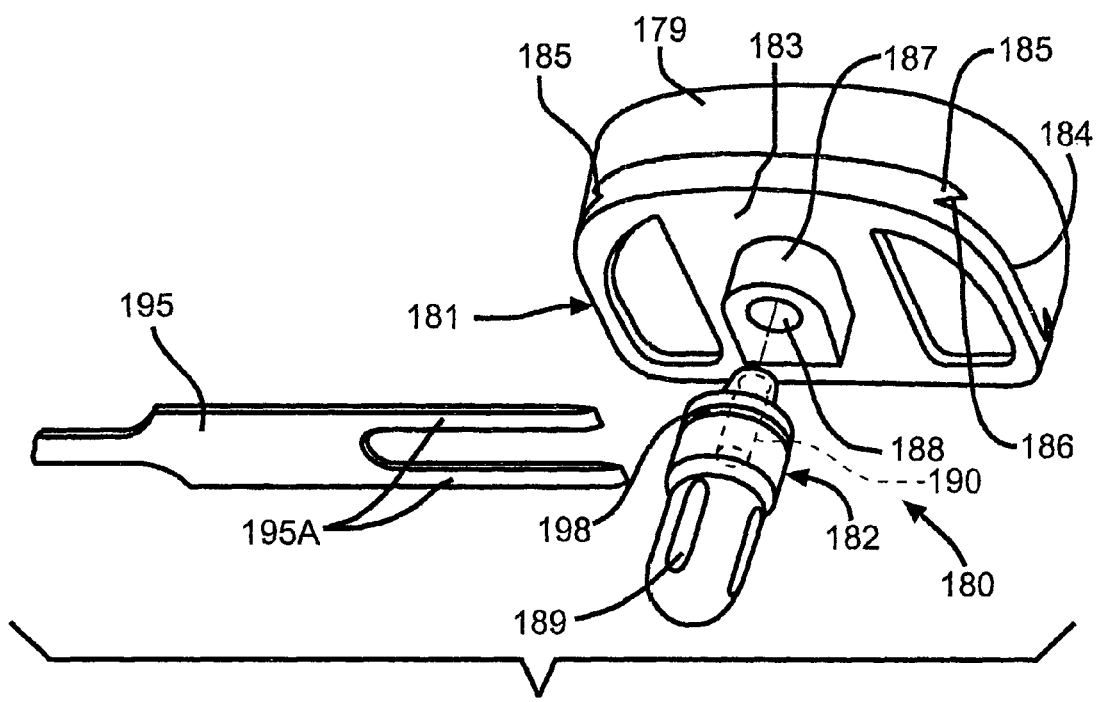
FIG. 20 is a perspective view of another embodiment of tibial component showing the stem portion thereof as a separate piece from the base.
Figure 21:
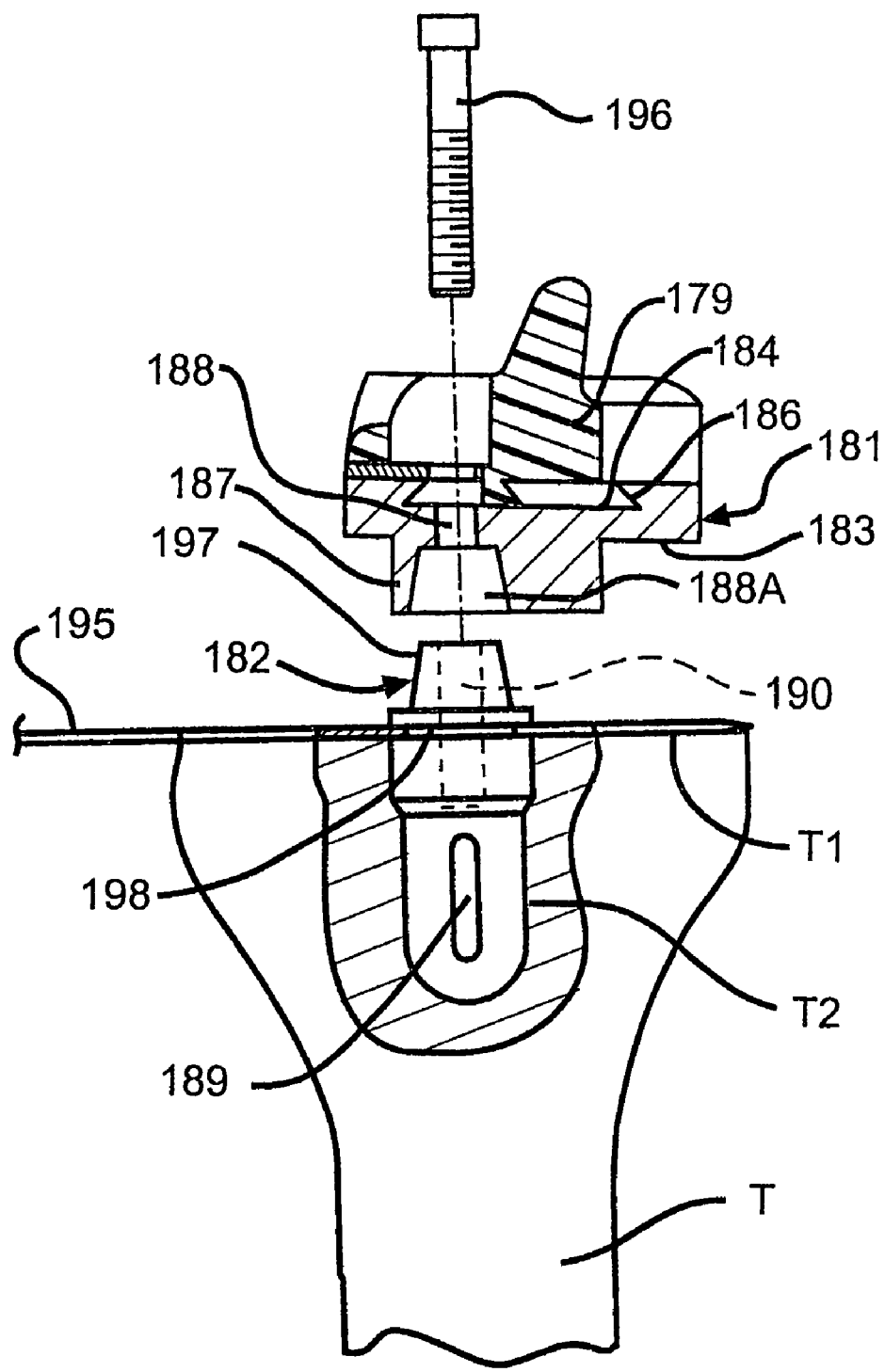
FIG. 21 is a side view of the tibial component of FIG. 20 showing its implantation in the proximal end of a prepared tibia.

Referring now to FIGS. 20 and 21, there is shown another embodiment of tibial component 180 along with a tool 195 for use in implanting such tibial component in the proximal end of a prepared tibia T. The tibial component 180 includes a tibial base 181, a tibial stem 182 and a plastic insert 179 engaged to the tibial base 181. The tibial base 181 has an inferior surface 183 intended to engage the prepared proximal end of the tibia T and a superior surface 184 to which may be affixed a plastic insert 179 contoured to be engaged by a femoral component. The tibial base 181 has raised areas 185 along the anterior and posterior edges. Each of the raised areas is provided with an undercut wall surface 186 defining grooves for receiving and retaining the plastic insert 179.

Extending distally from the inferior surface 183 is an extension 187. The tibial base 181 has a central passageway 188 extending from the superior surface 184 and through the extension 187. The extension 187 and the passageway 188 may be disposed at an angle of up to 10° relative to a line perpendicular to the superior surface 184 in order to accommodate the anatomy of the patient.

The tibial stem 182 is provided with a recess 190 sized and positioned to become an extension of the passageway 188 of the tibial base 181. The recess 190 may be threaded for engagement by a threaded screw 196 extending through the plastic insert 179 and its articular surface and through the passageway 188 to join the tibial stem 182 to the tibial base 181. As shown in FIG. 21, the distal end 188A of the passageway 188 may be tapered to define a Morse taper cavity. The tibial stem 182 is also provided, at its proximal end, with a Morse taper extension 197 sized to snugly engage the Morse taper cavity at the distal end 188A of the passageway 188. The tibial stem 182 is also provided with a plurality of outwardly facing grooves 189 to assist in fixation.

In preparing the proximal end of the tibia T to receive the tibial component 180, the proximal end T1 of the tibia is cut to form substantially a flat surface. A cavity T2 is formed to receive the tibial stem 182. Since the cavity T2 may be oversized, the tibial stem 182 is provided with an annular groove 198 sized to receive the tines 195A of the tool 195. As can be seen in FIG. 21, with the tines 195A engaged in the groove 198, the tool 195 can support the tibial stem 182 at the proper location relative to the prepared proximal end T1 of the tibia T until such time as the screw 196 is engaged in the threaded recess 190 to support such tibial stem 182 on the tibial base 181.

In implanting the tibial stem 163 of the embodiment of FIGS. 18 and 18A, a tool similar to the tool 195 may be used to engage the grooves 270 to support the stem 163 until it is engaged by the screw 158 or 258.

In each of the embodiments of FIGS. 18, 18A, 19, 20 and 21, it is preferred that the surface of the tibial base which is to be contacted by a plastic insert be polished to a high degree, on the order of four (4) rms or less, to prevent premature wear on the surface of the plastic insert engaged to the tibial base.

Description of Surgical Procedure

A medial parapatellar incision is made from the superior pole of the patella to the tibial tuberosity. Medial parapatellar arthrotomy is made from the inferior edge of the vastus medial is to the tibial tuberosity. A subvastus or mid vastus arthrotomy may be utilized, based upon patient anatomy or surgeon experience.

The knee is place in extension and the patella excised without eversion, using a patellar clamp inserted into the prepatellar bursa, to prevent damage to the anterior skin.

An extramedullary tibial alignment guide is placed along the medial or lateral half of the tibia and secured with fixation pins. An extramedullary alignment guide of the type disclosed in U.S. application Ser. No. 09/973,584 filed Oct. 9, 2001, assigned to the assignee of the present invention and incorporated herein by reference, is fixed to the femur after performing the extramedullary alignment procedure, and the distal femoral cut is made at the appropriate depth and angle of the implant, nominally 6° valgus and 10-12 mm depth of cut. As an alternative, an intramedullar alignment guide system could be used. This cut is taken all the way across both distal femoral condyles, rather than being unicondylar in nature. This cut is made at 90° to the femoral shaft.

The tibial component is implanted first. The fixation surface is coated with cement, and the modular tibial stem is driven through the reverse Morse taper to lock the tibial stem to the bone.

The anterior flange component is then implanted, followed by the lateral then medial condyles. Once all pieces are loosely assembled inside the knee and proper alignment is assured, the locking pin is inserted from the side and rigidly fixes the components together. Final impaction is then accomplished.

Lastly, the patella is cemented in place.

After all cement has hardened and excess is removed, the final poly slides in from the side, and is secured with an AP locking clip or screw, which also helps lock the modular stem in place.

Routine closure is performed, and rapid rehab program initiated.

The above detailed description of the present invention is given for explanatory purposes. It will be apparent to those skilled in the art that numerous changes and modifications can be made without departing from the scope of the invention.

We claim:

1. A method of performing knee arthroplasty comprising the steps of:
   (a) providing a multi-piece tibial component, the tibial component including
      (i) a tibial base having an inferior surface for engagement with a prepared surface at the proximal end of a tibia and a passageway extending through the base, the passageway including an open proximal end, an open distal end, and a portion which tapers inwardly in a distal direction, the tibial base further including an enlarged threaded aperture adjacent said superior surface and defining a shoulder extending outwardly from the portion which tapers inwardly, and (ii) a tibial stem including a tapered extension shaped to snugly engage the tapered portion of the passageway and a threaded flange portion shaped to threadably engage the enlarged threaded aperture of the tibial base, the threaded flange positioned proximal of the tapered extension;

(b) preparing the proximal end of a tibia including forming a cavity along the intramedullary canal of the tibia;

(c) positioning the tibial base on the prepared tibia proximal end;

(d) thereafter positioning the tibial stem through the passageway in the tibial base, wherein a portion of the tibial stem is retained within the passageway and a portion of the tibial stem extends distally from the open distal end of the passageway and into the prepared cavity; and (e) securing the tibial base and the tibial stem together by threadably engaging the threaded flange portion of the tibial stem with the threaded aperture of the tibial base, such that the tapered extension of the tibial stem is lockingly engaged with the passageway of the tibial base, said step of securing the tibial base including leaving a gap between a distal side of the threaded flange and a proximal surface of the shoulder to ensure that the threadably engaging step effects locking engagement of the tapered extension and tibial base.

2. The method of claim 1 wherein the tibial base has inwardly facing threads and the tibial stem has outwardly facing threads proximally of the tapered extension and further including the step of engaging the outwardly facing threads to the inwardly facing threads.

3. The method of claim 2 wherein the tibial component further includes an insert engageable with the base, the insert having a passageway and the tibial stem extension having a threaded cavity and further extending a screw through the insert passageway and engaging it in the extension threaded cavity.

4. A method for anchoring a tibial implant to a proximal tibia, the method comprising the steps of:

seating a tibial plate on the proximal tibia, the tibial plate having a passageway extending therethrough, the passageway having an open proximal end and an open distal end, the open proximal end having a threaded aperture formed therein, the threaded aperture defining a shoulder extending outwardly from the passageway;

extending an elongated member through the tibial plate and into the tibia after the step of seating a tibial plate on the proximal tibia, the elongated member having a proximal end with a threaded flange portion and a distal end, wherein the proximal end of the elongated member is positioned within the passageway and the distal end of the elongated member extends distally from the open distal end of the passageway;

securing the elongated member to the tibial plate by threadably engaging the threaded flange portion of the elongated member with the threaded aperture of the tibial plate, said step of securing effecting a taper lock between a tapered portion of the elongated member and a correspondingly tapered portion of the passageway, such that a gap remains between a distal side of the threaded flange and a proximal surface of the shoulder, whereby firm locking engagement of the tapered extension and tibial base is ensured by said threadably engaging step;

mounting a tibio-femoral insert to the tibial plate; and inserting a screw through the tibio-femoral insert and into threaded engagement with a socket formed in the elongated member to retain the tibio-femoral insert on the tibial plate.

5. The method of claim 4, wherein extending an elongated member through the tibial plate includes threadably engaging the elongated member with the tibial plate.

* * * * *